US008658171B2

(12) United States Patent
Zhu et al.

(10) Patent No.: US 8,658,171 B2
(45) Date of Patent: Feb. 25, 2014

(54) HUMANIZED ANTI-TNFα ANTIBODIES

(75) Inventors: Baoguo Zhu, Guangdong (CN);
Desheng Tao, Guangdong (CN); Bill Nai-Chau Sun, Shanghai (CN);
Lee-Hwei King Sun, Shanghai (CN);
Ruey Shyan Liou, Shanghai (CN);
Cecily Rou-Yun Sun, Shanghai (CN);
Qiang Li, Shanghai (CN); Yucai Peng, Guangdong (CN); Jingwei Zhang, Guangdong (CN); Zhenxiang Hu, Guangdong (CN)

(73) Assignee: Livzon Mabpharm Inc., Zhuhai, Guangdong (CN)

( * ) Notice: Subject to any disclaimer, the term of this patent is extended or adjusted under 35 U.S.C. 154(b) by 0 days.

(21) Appl. No.: 13/405,144

(22) Filed: Feb. 24, 2012

(65) Prior Publication Data

US 2012/0219547 A1    Aug. 30, 2012

(30) Foreign Application Priority Data

Feb. 28, 2011  (CN) .......................... 2011 1 0048505
Feb. 7, 2012   (CN) .......................... 2012 1 0026698
Feb. 13, 2012  (WO) ................ PCT/CN2012/071079

(51) Int. Cl.
*A61K 38/00* (2006.01)

(52) U.S. Cl.
USPC ................. 424/133.1; 424/142.1; 424/143.1; 435/328; 435/331

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,275,149 A | 6/1981 | Litman et al. | |
| 4,318,980 A | 3/1982 | Boguslaski et al. | |
| 4,376,110 A | 3/1983 | David et al. | |
| 4,737,456 A | 4/1988 | Weng et al. | |
| 4,818,679 A | 4/1989 | Chasin et al. | |
| 5,179,017 A | 1/1993 | Axel et al. | |
| 5,231,024 A | 7/1993 | Moeller et al. | |
| 5,919,452 A | 7/1999 | Le et al. | |
| 6,054,297 A * | 4/2000 | Carter et al. ................. | 435/69.6 |
| 7,524,502 B2 | 4/2009 | Hellendoorn et al. | |

FOREIGN PATENT DOCUMENTS

| | | | |
|---|---|---|---|
| CN | 1510052 A | | 7/2004 |
| CN | 1544466 A | | 11/2004 |
| CN | 1585778 A | | 2/2005 |
| CN | 101111521 A | | 1/2008 |
| CN | 101177453 A | * | 5/2008 |
| WO | WO 92/16553 A1 | | 10/1992 |
| WO | WO 2005/047329 A1 | | 5/2005 |
| WO | WO 2006/071091 A1 | | 7/2006 |

OTHER PUBLICATIONS

Burgess et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, 1990, J Cell Biol, vol. 111, p. 2129-2138.*
Lazar et al., Transforming growth factor alpha: mutation of aspartic acid 47 and leucine 48 results in different biological activities, Mol Cell Biol, vol. 8, p. 1247-1252.*
Padlan et al, Identification of Specificity-Determining Residues in Antibodies, 1995, FASEB J, vol. 9, p. 133-139.*
Burgess et al (J Cell Biol, 1990, 111:2129-2138).*
Lazar et al (Mol Cell Biol, 1998, 8:1247-1252).*
(Padlan et al, FASEB J, 1995, 9:133-139).*
Roguska et al (Proc Natl Acad Sci, 1994, 91:969-973).*
International Patent Application No. PCT/CN2012/071079: International Search Report, mailed May 3, 2012, with English translation.
Kaufman et al., "Amplification and Expression of Sequences Cotransfected with a Modular Dihydrofolate Reductase Complementary DNA Gene" *J. Mol. Biol.*, 159:601-621 (1982).
Möller et al., "Monoclonal Antibodies to Human Tumor Necrosis Factor α: in vitro and in vivo Application" *Cytokine*, 2:162-169 (1990).
O'Sullivan et al., "Methods for the Preparation of Enzyme-Antibody Conjugates for Use in Enzyme Immunoassay" *Methods in Enzymol.*, 73:147-166 (1981).
Pennica et al., "Human Tumor Necrosis Factor: Precursor Structure, Expression and Homology to Lymphotoxin" *Nature*, 312:724-729 (1984).
Suthanthiran et al., "Renal Transplantation" *N. Engl. J. Med.*, 331:365-375 (1994).
Yanisch-Perron et al., "Improved M13 Phage Cloning Vectors and Host Strains: Nucleotide Sequences of the M13mp18 and pUC19 Vectors" *Gene*, 33:103-119 (1985).
Zola, *Monoclonal Antibodies: A Manual of Techniques*, CRC Press, Inc., 1987; pp. 147-158.

\* cited by examiner

*Primary Examiner* — Sean E Aeder
*Assistant Examiner* — Julie Wu
(74) *Attorney, Agent, or Firm* — Finnegan, Henderson, Farabow, Garrett & Dunner LLP.

(57) ABSTRACT

The present invention provides a humanized anti-TNF monoclonal antibody and the use thereof. The humanized anti-TNF monoclonal antibody significantly reduces the immunogenicity of murine-antibody while retaining the ability of antibody to recognize antigen, compared with conservative mouse chimeric antibody. Therefore, safety of the antibody in clinical applications has been improved.

8 Claims, 3 Drawing Sheets

SEQUENCE LISTING

```
<160> NUMBER OF SEQ ID NOS: 35

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      antibody heavy chain variable region polypeptide

<400> SEQUENCE: 1

Gln Val Gln Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr His Tyr
            20                  25                  30

Gly Met His Trp Val Lys Gln Thr Pro Gly Arg Gly Leu Lys Trp Val
        35                  40                  45

Gly Trp Ile Asn Thr Tyr Thr Gly Glu Pro Thr Tyr Asp Ala Asp Phe
    50                  55                  60

Gln Gly Arg Phe Thr Phe Ser Leu Glu Thr Ser Val Ser Thr Ala Phe
65                  70                  75                  80

Leu Gln Ile Asn Ser Leu Lys Asp Glu Asp Leu Ala Thr Tyr Phe Cys
                85                  90                  95

Ala Arg Tyr Asp Phe Asp Gly Phe Asp Tyr Trp Gly Gln Gly Thr Thr
            100                 105                 110

Leu Thr Val Ser Ser
        115

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      antibody light chain variable region polypeptide

<400> SEQUENCE: 2

Glu Asn Val Leu Thr Gln Ser Pro Pro Ile Leu Ser Ala Ser Pro Gly
1               5                   10                  15

Glu Arg Val Thr Met Thr Cys Arg Ala Ser Ser Ser Ile Thr Phe Asn
            20                  25                  30

Tyr Leu His Trp Tyr Gln Gln Lys Ser Gly Asp Ser Pro Lys Val Trp
            35                  40                  45
```

```
Ile Tyr Ser Thr Ser Asn Leu Val Ser Gly Val Pro Ser Arg Phe Ser
 50                  55                  60

Gly Ser Gly Ser Gly Thr Ser Tyr Ser Leu Thr Ile Ser Ser Leu Glu
 65                  70                  75                  80

Ala Glu Asp Ala Ala Thr Tyr Tyr Cys Gln Gln Tyr Ser Asp Tyr Pro
                 85                  90                  95

Tyr Thr Phe Gly Gly Gly Thr Lys Leu Glu Ile Lys
            100                 105

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      antibody heavy chain complementary determining
      region CDR-H1 peptide

<400> SEQUENCE: 3

His Tyr Gly Met His
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody heavy chain complementary determining
      region CDR-H2 peptide

<400> SEQUENCE: 4

Trp Ile Asn Thr Tyr Thr Gly Glu Pro Thr Tyr Asp Ala Asp Phe Gln
1               5                   10                  15

Gly

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      antibody heavy chain complementary determining
      region CDR-H3 peptide

<400> SEQUENCE: 5

Tyr Asp Phe Asp Gly Phe Asp Tyr
1               5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      antibody light chain complementary determining
      region CDR-L1 peptide

<400> SEQUENCE: 6

Arg Ala Ser Ser Ser Ile Thr Phe Asn Tyr Leu His
1               5                   10

<210> SEQ ID NO 7
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      antibody light chain complementary determining
      region CDR-L2 peptide

<400> SEQUENCE: 7

Ser Thr Ser Asn Leu Val Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody light chain complementary determining
      region CDR-L3 peptide

<400> SEQUENCE: 8

Gln Gln Tyr Ser Asp Tyr Pro Tyr Thr
1               5

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Glu or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (20)..(20)
<223> OTHER INFORMATION: Ile or Val
<220> FEATURE:
<221> NAME/KEY: MOD_RES
<222> LOCATION: (38)..(38)
<223> OTHER INFORMATION: Lys or Arg
<220> FEATURE:
<221> NAME/KEY: MOD_RES
<222> LOCATION: (44)..(44)
<223> OTHER INFORMATION: Ser or Gly
<220> FEATURE:
<221> NAME/KEY: MOD_RES
<222> LOCATION: (69)..(69)
<223> OTHER INFORMATION: Thr or Val
<220> FEATURE:
<221> NAME/KEY: MOD_RES
<222> LOCATION: (73)..(73)
<223> OTHER INFORMATION: Glu or Asp
<220> FEATURE:
<221> NAME/KEY: MOD_RES
<222> LOCATION: (76)..(76)
<223> OTHER INFORMATION: Thr or Val
<220> FEATURE:
<221> NAME/KEY: MOD_RES
<222> LOCATION: (80)..(80)
<223> OTHER INFORMATION: Phe or Tyr
<220> FEATURE:
<221> NAME/KEY: MOD_RES
<222> LOCATION: (85)..(85)
<223> OTHER INFORMATION: Thr or Ser
<220> FEATURE:
<221> NAME/KEY: MOD_RES
<222> LOCATION: (93)..(93)
<223> OTHER INFORMATION: Thr or Val

<400> SEQUENCE: 9

Gln Val Gln Leu Val Gln Ser Gly Pro Glu Leu Lys Lys Pro Gly Xaa
```

```
                1               5                   10                  15
Xaa Val Lys Xaa Ser Cys Lys Ala Ser Gly Tyr Thr Pro Thr His Tyr
                    20                  25                  30

Gly Met His Trp Val Xaa Gln Thr Pro Gly Arg Xaa Leu Lys Trp Val
            35                  40                  45

Gly Trp Ile Asn Thr Tyr Thr Gly Glu Pro Thr Tyr Asp Ala Asp Phe
        50                  55                  60

Gln Gly Arg Phe Xaa Phe Ser Leu Xaa Thr Ser Xaa Ser Thr Ala Xaa
65                  70                  75                  80

Leu Gln Ile Asn Xaa Leu Lys Asp Glu Asp Leu Ala Xaa Tyr Phe Cys
                85                  90                  95

Ala Arg Tyr Asp Phe Asp Gly Phe Asp Tyr Trp Gly Gln Gly Thr Thr
                    100                 105                 110

Leu Thr Val Ser Ser
            115

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Met or Leu
<220> FEATURE:
<221> NAME/KEY: MOD_RES
<222> LOCATION: (18)..(18)
<223> OTHER INFORMATION: Glu or Arg
<220> FEATURE:
<221> NAME/KEY: MOD_RES
<222> LOCATION: (21)..(21)
<223> OTHER INFORMATION: Met or Ile
<220> FEATURE:
<221> NAME/KEY: MOD_RES
<222> LOCATION: (48)..(48)
<223> OTHER INFORMATION: Trp or Leu
<220> FEATURE:
<221> NAME/KEY: MOD_RES
<222> LOCATION: (61)..(61)
<223> OTHER INFORMATION: Ala or Ser
<220> FEATURE:
<221> NAME/KEY: MOD_RES
<222> LOCATION: (79)..(79)
<223> OTHER INFORMATION: Val or Leu
<220> FEATURE:
<221> NAME/KEY: MOD_RES
<222> LOCATION: (84)..(84)
<223> OTHER INFORMATION: Ala or Phe

<400> SEQUENCE: 10

Glu Asn Val Leu Thr Gln Ser Pro Pro Ile Xaa Ser Ala Ser Pro Gly
1               5                   10                  15

Glu Xaa Val Thr Xaa Thr Cys Arg Ala Ser Ser Ser Ile Thr Phe Asn
                20                  25                  30

Tyr Leu His Trp Tyr Gln Gln Lys Ser Gly Asp Ser Pro Lys Val Xaa
            35                  40                  45

Ile Tyr Ser Thr Ser Asn Leu Val Ser Gly Val Pro Xaa Arg Phe Ser
        50                  55                  60

Gly Ser Gly Ser Gly Thr Ser Tyr Ser Leu Thr Ile Ser Ser Xaa Glu
65                  70                  75                  80

Ala Glu Asp Xaa Ala Thr Tyr Tyr Cys Gln Gln Tyr Ser Asp Tyr Pro
                85                  90                  95
```

-continued

```
Tyr Thr Phe Gly Gly Gly Thr Lys Leu Glu Ile Lys
                100                 105

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      antibody framework region FR-H1 polypeptide
<220> FEATURE:
<221> NAME/KEY: MOD_RES
<222> LOCATION: (16)..(16)
<223> OTHER INFORMATION: Glu or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (20)..(20)
<223> OTHER INFORMATION: Ile or Val

<400> SEQUENCE: 11

Gln Val Gln Leu Val Gln Ser Gly Pro Glu Leu Lys Lys Pro Gly Xaa
1               5                   10                  15

Xaa Val Lys Xaa Ser Cys Lys Ala Ser Gly Tyr Thr Phe Thr
            20                  25                  30

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      antibody framework region FR-H2 peptide
<220> FEATURE:
<221> NAME/KEY: MOD_RES
<222> LOCATION: (3)..(3)
<223> OTHER INFORMATION: Lys or Arg
<220> FEATURE:
<221> NAME/KEY: MOD_RES
<222> LOCATION: (9)..(9)
<223> OTHER INFORMATION: Ser or Gly

<400> SEQUENCE: 12

Trp Val Xaa Gln Thr Pro Gly Arg Xaa Leu Lys Trp Val Gly
1               5                   10

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
      antibody framework region FR-H3 polypeptide
<220> FEATURE:
<221> NAME/KEY: MOD_RES
<222> LOCATION: (3)..(3)
<223> OTHER INFORMATION: Thr or Val
<220> FEATURE:
<221> NAME/KEY: MOD_RES
<222> LOCATION: (7)..(7)
<223> OTHER INFORMATION: Glu or Asp
<220> FEATURE:
<221> NAME/KEY: MOD_RES
<222> LOCATION: (10)..(10)
<223> OTHER INFORMATION: Thr or Val
<220> FEATURE:
<221> NAME/KEY: MOD_RES
<222> LOCATION: (14)..(14)
<223> OTHER INFORMATION: Phe or Tyr
<220> FEATURE:
<221> NAME/KEY: MOD_RES
```

```
<222> LOCATION: (19)..(19)
<223> OTHER INFORMATION: Thr or Ser
<220> FEATURE:
<221> NAME/KEY: MOD_RES
<222> LOCATION: (27)..(27)
<223> OTHER INFORMATION: Thr or Val

<400> SEQUENCE: 13

Arg Phe Xaa Phe Ser Leu Xaa Thr Ser Xaa Ser Thr Ala Xaa Leu Gln
1               5                   10                  15

Ile Asn Xaa Leu Lys Asp Glu Asp Leu Ala Xaa Tyr Phe Cys Ala Arg
            20                  25                  30

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      antibody framework region FR-L1 peptide
<220> FEATURE:
<221> NAME/KEY: MOD_RES
<222> LOCATION: (11)..(11)
<223> OTHER INFORMATION: Met or Leu
<220> FEATURE:
<221> NAME/KEY: MOD_RES
<222> LOCATION: (18)..(18)
<223> OTHER INFORMATION: Glu or Arg
<220> FEATURE:
<221> NAME/KEY: MOD_RES
<222> LOCATION: (21)..(21)
<223> OTHER INFORMATION: Met or Ile

<400> SEQUENCE: 14

Glu Asn Val Leu Thr Gln Ser Pro Pro Ile Xaa Ser Ala Ser Pro Gly
1               5                   10                  15

Glu Xaa Val Thr Xaa Thr Cys
            20

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      antibody framework region FR-L2 peptide
<220> FEATURE:
<221> NAME/KEY: MOD_RES
<222> LOCATION: (13)..(13)
<223> OTHER INFORMATION: Trp or Leu

<400> SEQUENCE: 15

Trp Tyr Gln Gln Lys Ser Gly Asp Ser Pro Lys Val Xaa Ile Tyr
1               5                   10                  15

<210> SEQ ID NO 16
<211> LENGTH: 32
<212> TYPE: PRT
<213> ORGANISM: Artificial Sequence
<220> FEATURE:
<223> OTHER INFORMATION: Description of Artificial Sequence: Synthetic
      antibody framework region FR-L3 polypeptide
<220> FEATURE:
<221> NAME/KEY: MOD_RES
<222> LOCATION: (4)..(4)
<223> OTHER INFORMATION: Ser or Ala
<220> FEATURE:
<221> NAME/KEY: MOD_RES
<222> LOCATION: (22)..(22)
<223> OTHER INFORMATION: Val or Leu
<220> FEATURE:
<221> NAME/KEY: MOD_RES
```

```
<222> LOCATION: (27)..(27)
<223> OTHER INFORMATION: Ala or Phe

<400> SEQUENCE: 16

Gly Val Pro Xaa Arg Phe Ser Gly Ser Gly Ser Gly Thr Ser Tyr Ser
1               5                   10                  15

Leu Thr Ile Ser Ser Xaa Glu Ala Glu Asp Xaa Ala Thr Tyr Tyr Cys
            20                  25                  30

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      5' primer FVHX

<400> SEQUENCE: 17
cgcgcaagct tcctcgag                                                 18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      3' primer RVCG

<400> SEQUENCE: 18
cgatgggccc ttggtgga                                                 18

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      5' primer HUCGF

<400> SEQUENCE: 19
accaagggcc catcggtctt c                                             21

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      3' primer HUCGE

<400> SEQUENCE: 20
cggaattctc atttacccgg agacaggga                                     29

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      3' primer VKCKO

<400> SEQUENCE: 21
agatggtgca gccacagttc gcttgatctc cagcttggtg cc                      42

<210> SEQ ID NO 22
<211> LENGTH: 21
<212> TYPE: DNA
```

<213> ORGANISM: Artificial Sequence
<220> FEATURE:
<223> OTHER INFORMATION: Description of Artificial Sequence: Synthetic
      5' primer HuCKF

<400> SEQUENCE: 22
gtggctgcac catctgtctt c                                           21

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      3' primer HUCKB

<400> SEQUENCE: 23
tgcggatccc taacactctc ccctgttgaa                                  30

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      5' primer

<400> SEQUENCE: 24
cgactggagc acgaggacac tga                                         23

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      3' primer

<400> SEQUENCE: 25
tccaggggcc agtggataga gaga                                        24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      3' primer

<400> SEQUENCE: 26
cactggatgg tgggaagatg gata                                        24

<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      antibody heavy chain variable region polypeptide

<400> SEQUENCE: 27

Gln Val Gln Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr His Tyr
            20                  25                  30

Gly Met His Trp Val Lys Gln Thr Pro Gly Arg Gly Leu Lys Trp Val
        35                  40                  45

Gly Trp Ile Asn Thr Tyr Thr Gly Glu Pro Thr Tyr Asp Ala Asp Phe
            50                  55                  60

Gln Gly Arg Phe Thr Phe Ser Leu Asp Thr Ser Val Ser Thr Ala Phe
65                  70                  75                  80

Leu Gln Ile Asn Ser Leu Lys Asp Glu Asp Leu Ala Val Tyr Phe Cys
                85                  90                  95

Ala Arg Tyr Asp Phe Asp Gly Phe Asp Tyr Trp Gly Gln Gly Thr Thr
            100                 105                 110

Leu Thr Val Ser Ser
        115

<210> SEQ ID NO 28
<211> LENGTH: 117
<212> TYPE: PRT
<213> ORGANISM: Artificial Sequence
<220> FEATURE:
<223> OTHER INFORMATION: Description of Artificial Sequence: Synthetic
      antibody heavy chain variable region polypeptide

<400> SEQUENCE: 28

Gln Val Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr His Tyr
            20                  25                  30

Gly Met His Trp Val Lys Gln Thr Pro Gly Arg Gly Leu Lys Trp Val
        35                  40                  45

Gly Trp Ile Asn Thr Tyr Thr Gly Glu Pro Thr Tyr Asp Ala Asp Phe
    50                  55                  60

Gln Gly Arg Phe Thr Phe Ser Leu Glu Thr Ser Thr Ser Thr Ala Tyr
65                  70                  75                  80

Leu Gln Ile Asn Ser Leu Lys Asp Glu Asp Leu Ala Thr Tyr Phe Cys
                85                  90                  95

Ala Arg Tyr Asp Phe Asp Gly Phe Asp Tyr Trp Gly Gln Gly Thr Thr
            100                 105                 110

Leu Thr Val Ser Ser
        115

<210> SEQ ID NO 29
<211> LENGTH: 117
<212> TYPE: PRT
<213> ORGANISM: Artificial Sequence
<220> FEATURE:
<223> OTHER INFORMATION: Description of Artificial Sequence: Synthetic
      antibody heavy chain variable region polypeptide

<400> SEQUENCE: 29

Gln Val Gln Leu Val Gln Ser Gly Pro Glu Leu Lys Lys Pro Gly Ala
1               5                   10                  15

Thr Val Lys Val Ser Cys Lys Ala Ser Gly Tyr Thr Phe Thr His Tyr
            20                  25                  30

Gly Met His Trp Val Lys Gln Thr Pro Gly Arg Ser Leu Lys Trp Val
        35                  40                  45

Gly Trp Ile Asn Thr Tyr Thr Gly Glu Pro Thr Tyr Asp Ala Asp Phe
    50                  55                  60

Gln Gly Arg Phe Thr Phe Ser Leu Glu Thr Ser Val Ser Thr Ala Phe
65                  70                  75                  80

Leu Gln Ile Asn Thr Leu Lys Asp Glu Asp Leu Ala Thr Tyr Phe Cys
                85                  90                  95

```
Ala Arg Tyr Asp Phe Asp Gly Phe Asp Tyr Trp Gly Gln Gly Thr Thr
            100                 105                 110

Leu Thr Val Ser Ser
        115

<210> SEQ ID NO 30
<211> LENGTH: 117
<212> TYPE: PRT
<213> ORGANISM: Artificial Sequence
<220> FEATURE:
<223> OTHER INFORMATION: Description of Artificial Sequence: Synthetic
      antibody heavy chain variable region polypeptide

<400> SEQUENCE: 30

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr His Tyr
            20                  25                  30

Gly Met His Trp Val Arg Gln Thr Pro Gly Arg Gly Leu Lys Trp Val
        35                  40                  45

Gly Trp Ile Asn Thr Tyr Thr Gly Glu Pro Thr Tyr Asp Ala Asp Phe
    50                  55                  60

Gln Gly Arg Phe Thr Phe Ser Leu Glu Thr Ser Val Ser Thr Ala Tyr
65                  70                  75                  80

Leu Gln Ile Asn Ser Leu Lys Asp Glu Asp Leu Ala Thr Tyr Phe Cys
                85                  90                  95

Ala Arg Tyr Asp Phe Asp Gly Phe Asp Tyr Trp Gly Gln Gly Thr Thr
            100                 105                 110

Leu Thr Val Ser Ser
        115

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic
      antibody light chain variable region polypeptide

<400> SEQUENCE: 31

Glu Asn Val Leu Thr Gln Ser Pro Pro Ile Leu Ser Ala Ser Pro Gly
1               5                   10                  15

Glu Glu Val Thr Met Thr Cys Arg Ala Ser Ser Ser Ile Thr Phe Asn
            20                  25                  30

Tyr Leu His Trp Tyr Gln Gln Lys Ser Gly Asp Ser Pro Lys Val Trp
        35                  40                  45

Ile Tyr Ser Thr Ser Asn Leu Val Ser Gly Val Pro Ala Arg Phe Ser
    50                  55                  60

Gly Ser Gly Ser Gly Thr Ser Tyr Ser Leu Thr Ile Ser Ser Leu Glu
65                  70                  75                  80

Ala Glu Asp Phe Ala Thr Tyr Tyr Cys Gln Gln Tyr Ser Asp Tyr Pro
                85                  90                  95

Tyr Thr Phe Gly Gly Gly Thr Lys Leu Glu Ile Lys
            100                 105

<210> SEQ ID NO 32
<211> LENGTH: 108
<212> TYPE: PRT
<213> ORGANISM: Artificial Sequence
<220> FEATURE:
<223> OTHER INFORMATION: Description of Artificial Sequence: Synthetic
``` antibody light chain variable region polypeptide

<400> SEQUENCE: 32

Glu Asn Val Leu Thr Gln Ser Pro Pro Ile Met Ser Ala Ser Pro Gly
1               5                   10                  15

Glu Arg Val Thr Met Thr Cys Arg Ala Ser Ser Ser Ile Thr Phe Asn
            20                  25                  30

Tyr Leu His Trp Tyr Gln Gln Lys Ser Gly Asp Ser Pro Lys Val Leu
        35                  40                  45

Ile Tyr Ser Thr Ser Asn Leu Val Ser Gly Val Pro Ser Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Asp Tyr Pro
                85                  90                  95

Tyr Thr Phe Gly Gly Gly Thr Lys Leu Glu Ile Lys
            100                 105

<210> SEQ ID NO 33
<211> LENGTH: 108
<212> TYPE: PRT
<213> ORGANISM: Artificial Sequence
<220> FEATURE:
<223> OTHER INFORMATION: Description of Artificial Sequence: Synthetic
      antibody light chain variable region polypeptide

<400> SEQUENCE: 33

Glu Asn Val Leu Thr Gln Ser Pro Pro Ile Leu Ser Ala Ser Pro Gly
1               5                   10                  15

Glu Arg Val Thr Leu Thr Cys Arg Ala Ser Ser Ser Ile Thr Phe Asn
            20                  25                  30

Tyr Leu His Trp Tyr Gln Gln Lys Ser Gly Asp Ser Pro Lys Val Trp
        35                  40                  45

Ile Tyr Ser Thr Ser Asn Leu Val Ser Gly Val Pro Ala Arg Phe Ser
    50                  55                  60

Gly Ser Gly Ser Gly Thr Ser Tyr Ser Leu Thr Ile Ser Ser Leu Glu
65                  70                  75                  80

Ala Glu Asp Ala Ala Thr Tyr Tyr Cys Gln Gln Tyr Ser Asp Tyr Pro
                85                  90                  95

Tyr Thr Phe Gly Gly Gly Thr Lys Leu Glu Ile Lys
            100                 105

<210> SEQ ID NO 34
<211> LENGTH: 117
<212> TYPE: PRT
<213> ORGANISM: Artificial Sequence
<220> FEATURE:
<223> OTHER INFORMATION: Description of Artificial Sequence: Synthetic
      antibody heavy chain variable region polypeptide

<400> SEQUENCE: 34

Gln Val Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Gly Met His Trp Val Lys Gln Thr Pro Gly Arg Ser Leu Lys Trp Val
        35                  40                  45

Gly Trp Ile Asn Thr Tyr Thr Gly Glu Pro Thr Tyr Asp Ala Asp Phe
    50                  55                  60

```
Gln Gly Arg Phe Thr Phe Ser Leu Glu Thr Ser Thr Ser Thr Ala Phe
65                  70                  75                  80

Leu Gln Ile Asn Thr Leu Lys Asp Glu Asp Leu Ala Thr Tyr Phe Cys
                85                  90                  95

Ala Arg Tyr Asp Phe Asp Gly Phe Asp Tyr Trp Gly Gln Gly Thr Thr
                100                 105                 110

Leu Thr Val Ser Ser
            115

<210> SEQ ID NO 35
<211> LENGTH: 108
<212> TYPE: PRT
<213> ORGANISM: Artificial Sequence
<220> FEATURE:
<223> OTHER INFORMATION: Description of Artificial Sequence: Synthetic
      antibody light chain variable region polypeptide

<400> SEQUENCE: 35

Glu Asn Val Leu Thr Gln Ser Pro Pro Ile Met Ser Ala Ser Pro Gly
1               5                   10                  15

Glu Glu Val Thr Met Thr Cys Arg Ala Ser Ser Ser Ile Thr Phe Asn
                20                  25                  30

Tyr Leu His Trp Tyr Gln Gln Lys Ser Gly Asp Ser Pro Lys Val Trp
            35                  40                  45

Ile Tyr Ser Thr Ser Asn Leu Val Ser Gly Val Pro Ala Arg Phe Ser
        50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Asp Tyr Pro
                85                  90                  95

Tyr Thr Phe Gly Gly Gly Thr Lys Leu Glu Ile Lys
                100                 105
```

HUMANIZED ANTI-TNFα ANTIBODIES

CROSS REFERENCE TO RELATED APPLICATIONS

This application claims priority to Chinese Patent Application No. CN 201110048505.1, filed Feb. 28, 2011; Chinese Patent Application No. CN 201210026698.5, filed Feb. 7, 2012; and International Patent Application No. PCT/CN2012/071079, filed Feb. 13, 2012. The entire contents of each of the above-identified applications are hereby incorporated by reference.

TECHNICAL FIELD

The present invention relates to at least a humanized anti tumor necrosis factor-α (TNFα) or fragments thereof, including specific parts or variants, and nucleic acid encoding the humanized anti-TNFα antibody and its complementary nucleic acid, vectors, host cells, and the preparation method thereof, and compositions and kits comprising the humanized anti-TNFα antibody, and the use thereof.

BACKGROUND

Human tumor necrosis factor-α (TNFα) is a proinflammatory cytokine produced by monocytes and macrophages, which is a 26 kDA precursor protein when initially produced with N terminal inside the cells and C terminal outside the cells, named transmembrane type TNFα. Pennica et al. cloned TNFα gene cDNA for the first time in 1984, and deduced that human TNFα molecule is composed of 157 amino acid residues, and weights about 17 KD (Pennica D, et al, Nature 1984; 312:724). Huamn TNF has two molecular forms, TNFα and TNFβ. TNFα is produced by activated macrophages or monocytes, and causes neoplastic tissues hengrrhagie necrosis, thus it is also called Cachectin. TNFβ is mainly secreted by active T lymphocytes. Both have similar pyretogenesis. TNFα acts on receptors on the surface of oncocytes, and breaks into lysosome by identifying the cell, binding and endocytosing, and then activates lysosomes and proteases to cause cell death. TNFα plays an important role in immune response, inflammation, and response to injury, majorly affects the regulation of cell proliferation and cell apoptosis. Besides the effects on tumor cell such as cytotoxicity, cytolysis, induction of apoptosis and cell proliferation suppression, TNFα also can facilitate cell differentiation of myeloid leukemia cell to macrophage, and improve the phagocytic activity of neutrophile granulocyte.

An appropriate amount of TNFα can activate immune system to enhance immunity of the body, and play an important role in defense system of host resisting microbial invasion and tumor inhibition. But when over expressed, TNFα may cause several pathologic damages with other inflammatory factors. Therefore, the activities of TNFα may be suppressed or neutralized at different levels to block it from approaching receptors, in turn avoid the consequence of signal transduction.

For the purpose of overcoming relevant problems caused by using non-human antibodies, it is a relatively effective strategy of treatment to construct human-murine chimeric antibody to decrease organism immunogenicity initiated by HAMA. Such kind of chimeric antibody is made by incorporating non-human antibody variable region into human antibody constant region while retaining amino acid sequences of original heavy chain, light chain variable regions of non-human antibody (see, Daddona, P. E et al. PCT publication WO92/16553, Le, J. et al., U.S. Pat. No. 5,919,452, Kang, Heui H et al. PCT publication WO2005/047329, Jin BOquan et al. Chinese patent publication CN1544466A), Jin Yihui et al. Chinese patent publication CN101177453 provides a chimeric antibody which can bind to human tumor necrosis factor. Compared to non-human antibody, the immunogenicity of the chimeric antibody decreases, however, it may cause HAMA response in varied degrees since the murine derived portion in the chimeric antibody is still high, specifically including skin mucosa reaction, allergic reaction, arrhythmia and stenocardia, renal insufficiency, even coma when severe. Therefore, the clinical applications of this kind of chimeric antibodies are greatly limited.

Clinical trials demonstrate that this kind of chimeric antibodies as heterogeneous protein may cause immunological rejecting response of the heterogeneous protein by organism immune system (i.e., Human anti mouse antibody, HAMA response) when administrated to human. The response leads to rapid clearance of the murine antibody in human bodies, and short half life. Repeated administration may even result in severe anaphylactic shock. Moreover, the "foreign" antibody may be attacked by immune antibody, so that they may be neutralized before presenting pharmaceutical effects.

The inventors develop a new technique to prepare humanized antibody by utilizing genetic technology for the purpose of reducing the murine derived portion to minimum in the chimeric antibody on the basis of aforesaid patents. The technique comprises separately incorporating complementary determining regions (CDRs) of murine antibody heavy chain variable region and light chain variable region into human antibody framework region (FR). The obtained humanized antibody is similar to human sequence in structure as possible, meantime, it also can maintain CDR conformation similar to parent non-human antibody. Compared to parent non-human antibody and chimeric antibody, the portion of parent non-human amino acid sequence in the engineered humanized antibody decreases, one hand, the ability of antibody recognizing antigen is remained; the other hand, the immunogenicity of murine antibody has been greatly decreased. Therefore, safety of the antibody in clinical applications has been improved.

Consequently, the present invention provides a humanized antibody, which is safer, has longer half life more significant effects in human body, compared to murine chimeric antibody in prior arts.

SUMMARY OF THE INVENTION

In one aspect, the present invention provides at least one humanized anti tumor necrosis factor monoclonal antibody, or specified complementary determining regions, heavy chain or light chain variable region, heavy chain or light chain constant region, framework region, or any other arbitrary parts, thereof. The antibody of the present invention may be derived from any mammals, for example, but not limited to human, mouse, rat, rodent, primate or any combination thereof.

The antibody of the present invention specifically binds to at least one epitope of TNF proteins, subunit, fragment, part thereof, or any combination thereof. The said at least one epitope may comprise at least on antibody binding area. The said at least one epitope may optionally comprise at least one complementary determining area (CDR) (for example, heavy chain variable region or light chain variable region) and/or at least constant or variable framework region (FR) or any arbitrary part. The amino acid sequence of the said at least antibody may further optionally comprise insertion, deletion or conservatively substitution of at least one amino acid residue.

In another aspect, the present invention provides at least one nucleic acid molecules, the nucleic acid molecule comprises polynucleotide encoding at least one humanized anti tumor necrosis factor antibody of the present invention, or is complementary to or hybridized to the polynucleotide encoding at least one humanized anti tumor necrosis factor antibody of the present invention, wherein the antibody comprises at least one specific sequence, domain, part or variant thereof.

In another aspect, the present invention provides a recombinant vector comprising the nucleic acid molecule encoding the humanized anti tumor necrosis factor antibody, a host cell comprising the nucleic acid and/or recombinant vector, and the preparation method and/or use of the nucleic acid, vector and/or host cell.

At least one antibody of the present invention has at least one activity, for example, but not limited to neutralizing the toxicity of rhTNFα to L929 target cell, Suppressing and/or competing the binding of TNF with receptor and/or other monoclonal antibody for example, but not limited to Humira.

In another aspect, the present invention provide the use of antibody and/or composition of the present invention in inhibiting hTNFα activities, wherein the hTNFα related disease is selected for the group consisting of pyaemia, autoimmune diseases, malignant tumor, lung function disorder, transplant rejection, bacterial meningitis, cerebral malaria, AIDS and AIDS related complex (ARC), secondary cytomegalovirus infection after transplantation.

In another aspect, the present invention provides the use of in preparation of a medicament in diagnostic analysis of hTNFα, wherein the humanized anti tumor necrosis factor antibody also may be labeled by detecting molecule and/or may not be labeled, and the label comprises radioactive isotope; fluorescence label; various kinds of enzyme substrate mark.

In another aspect, the present provides the use of antibody and/or composition of the present invention in analysis method, wherein the analysis method includes competitive binding analysis, direct or indirect sandwich analysis, or immunoprecipitation analysis.

In another aspect, the present invention provide at least a composition, which comprises the humanized anti tumor necrosis antibody and/or its encoding nucleic acid, one or more auxiliaries selected from but not limited to pharmaceutically accepted vector, excipients, diluent, and additive. The composition may further optionally comprise at least one other antibody, nucleic acid, auxiliaries or any combination.

In another aspect, the present invention provides a kit comprising predetermined amount of reagents and instruction, the reagents comprise the antibody, nucleic acid and/or composition of the present invention. The kit further comprises other additives for example, but not limited to stabilizer, buffers.

BRIEF DESCRIPTION OF FIGURES

Persons skilled in the art may understand that the following figures are for the purpose of illustrating the present invention, which do not limit the scope of the present invention in any manners.

DETAILED DESCRIPTION OF THE INVENTION

Anti Tumor Necrosis Factor Antibody

Figure 1:
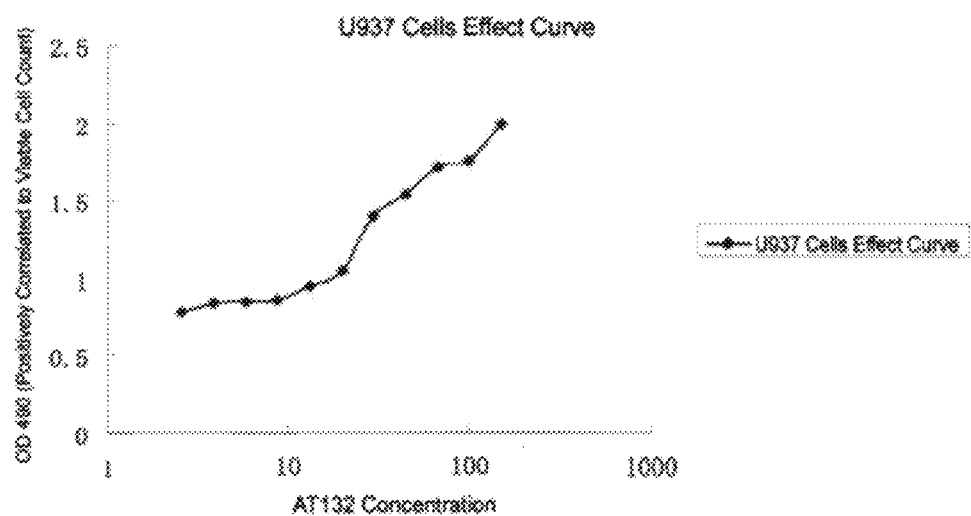
FIG. 1 shows the curve of the antibody neutralizing the effect of TNFα killing U937.

The antibody of the present invention comprises antibody amino acid sequence encoded by any suitable polynucleotide, or any separated or prepared antibody. The humanized antibody or antigen binding fragment preferably binds to human tumor necrosis factor, and as result, partially, substantially or completely neutralizes at least one activity of human tumor necrosis factor, consequently inhibits the signal transduction process and physiological process mediated by the binding of TNF with TNF receptor.

The humanized antibody of the present invention may be any type (IgG, IgA, IgM, IgE, IgD, et al.) or isotype, and may comprise κ or λ light chains, and α, μ, γ, ε or δ heavy chains.

At least one antibody of the present invention binds to at least one epitope of TNF protein, subunit, fragment, part thereof, or any combination thereof.

At least one anti tumor necrosis factor monoclonal antibody comprises following amino acid sequence, wherein the amino acid sequence of heavy variable region of the antibody is shown as SEQ ID NO: 1, and the amino acid sequence of light variable region of the antibody is shown as SEQ ID NO: 2.

```
SEQ ID NO: 1:
QVQLVQSGPELKKPGASVKISCKASGYTFTHYGMHWVKQTPGRGLK

WVGWINTYTGEPTYDADFQGRFTFSLETSVSTAFLQINSLKDEDLA

TYFCARYDFDGFDYWGQGTTLTVSS

SEQ ID NO: 2:
ENVLTQSPPILSASPGERVTMTCRASSSITFNYLHWYQQKSGDSPKVW

IYSTSNLVSGVPSRFSGSGSGTSYSLTISSLEAEDAATYYCQQYSDYP

YTFGGGTKLEIK
``` wherein complementary determining region CDR-H1 of the heavy chain variable region has a sequence of SEQ ID NO: 3; CDR-H2 has a sequence of SEQ ID NO: 4; CDR-H3 has a sequence of SEQ ID NO: 5; wherein, within framework region FR-H1, A can be substituted by E at amino acid residue position 16, S can be substituted by T at position 17, I can be substituted by V at position 20 (e.g., as shown in SEQ ID NO: 11); within FR-H2, K can be substituted by R at position 3, G can be substituted by S at position 9 (e.g., as shown in SEQ ID NO: 12); within FR-H3, T can be substituted by V at position 3, E can be substituted by D at position 7, V can be substituted by T at position 10, F can be substituted by Y at position 14, S can be substituted by T at position 19, T can be substituted by V at position 27 (e.g., as shown in SEQ ID NO: 13); and complementary determining region CDR-L1 has a sequence of SEQ ID NO: 6; CDR-L2 has a sequence of SEQ ID NO: 7; CDR-L3 has a sequence of SEQ ID NO: 8; wherein, within framework region FR-L1, L can be substituted by M at position 11, R can be substituted by E at position 18, M can be substituted by I at position 21 (e.g., as shown in SEQ ID NO: 14); within FR-L2, W can be by L at position 13 (e.g., as shown in SEQ ID NO: 15); within FR-L3, S can be substituted by A at position 4, L can be substituted by V at position 22, A can be substituted by F at position 27 (e.g., as shown in SEQ ID NO: 16).

SEQ ID NO. 3:
HYGMH

SEQ ID NO: 4:
WINTYTGEPTYDADFQG

SEQ ID NO: 5:
YDFDGFDY

SEQ ID NO: 6:
RASSSITFNYLH

SEQ ID NO: 7:
STSNLVS

SEQ ID NO: 8:
QQYSDYPYT

SEQ ID NO: 9:
QVQLVQSGPELKKPG(E/A)(T/S)VK(IN)SCKASGYTFTHYGMHWV(K/R)

QTPGR(S/G)LKWVGWINMGEPTYDADFQGRF(TN)FSL(E/D)TS(TN)STA(F/Y)LQIN (T/S)LKDEDLA(T/V)YFCARYDFDGFDYWGQGTTLTVSS

SEQ ID NO: 10:
ENVLTQSPPI(M/L)SASPGE(E/R)VT(M/I)TCRASSSITFNYLHWYQQKS

GDSPKV(W/L)IYSTSNLVSGVP(A/S)RFSGSGSGTSYSLTISS(V/L)EAED(NF)ATYYCQ

QYSDYPYTFGGGTKLEIK

SEQ ID NO: 11:
QVQLVQSGPELKKPG(E/A)(T/S)VK(IN)SCKASGYTFT

SEQ ID NO: 12:
WV(K/R)QTPGR(S/G)LKWVG

SEQ ID NO: 13 :
RF(TN)FSL(E/D)TS(TN)STA(F/Y)LQIN(T/S)LKDEDLA(TN)YFCAR

SEQ ID NO: 14:
ENVLTQSPPI(M/L)SASPGE(E/R)VT(M/I)TC

SEQ ID NO: 15:
WYQQKSGDSPKV(W/L)IY

SEQ ID NO: 16:
GVP(S/A)RFSGSGSGTSYSLTISS(V/L)EAED(A/F)ATYYC

In an embodiment of the present invention, the heavy chain constant region sequence of the humanized anti tumor necrosis factor antibody is the heavy chain constant region of human IgG1.

In an embodiment of the present invention, the light chain constant region sequence of the humanized anti tumor necrosis factor antibody is the light chain constant region of human antibody.

In a preferred embodiment of the present invention, the amino acid sequence of humanized anti tumor necrosis factor monoclonal antibody may be modified by inserting, deleting or conservatively substituting one or more amino acid residues, preferably 1-5 amino acid residues.

The monoclonal antibody modified or mutated by one or more insertion, deletion or conservatively substitution in any combinational forms may have differences in the amino acid sequences. In the preferred variant, the modification is obtained by amino acid conservative substitution from the aforesaid monoclonal antibody of the present invention. The conservative substation means a specific amino acid is substituted by another amino acid with similar properties. The amino acids below listed in non-limited manners are considered as conservatively exchangeable (with similar properties): a) alanine, serine and threonine; b) glutamic acid and aspartic acid; c) asparagine and glutamine; d) arginine and lysine; e) isoleucine, leucylacid, methionine and valine; and f) phenylalanine, tyrosine and tryptophan.

The functionally equivalent monoclonal antibody of the present invention is a variant, wherein one or more amino acid residues, preferably 1-5 amino acid residues are conservatively substituted. The conservative substitution includes: any one of aromatic amino acids Ala, Val, Leu and Ile can be substituted by another; hydroxyl residues Ser and Thr are exchangeable; acid residues Asp and Glu are exchangeable; amide residues Asn and Glun are exchangeable; basic residues Lys and Arg are exchangeable; aromatic residues Phe and Tyr are exchangeable.

Furthermore, present invention discloses the amino acid sequences which have at least 50% identity with the amino acid sequences of the present invention, or fragment thereof, and amino acid sequences with equivalent functions. In one embodiment, the amino acid sequences have at least 75% identity with the amino acid sequence SEQ ID NO:1 or 2 according to present invention, more preferably at least 85% identity, even more preferably at least 90% identity, even more preferably at least 95% identity, even more preferably at least 97% identity, and most preferably at least 99% identity.

Several kinds of antibodies are encompassed by present invention. For example, anti hTNFα antibody may be full-length antibody (for example, comprising complete human Fc region); or antibody fragment (for example, Fv, scFv, Fab, Fab' and (Fab')2). Moreover, the antibody can be labeled with detectable labels, fixed on solid phase carrier, and/or coupled with heterologous compounds (such as cytotoxin materials).

Fab is produced by treating IgG antibody molecule by protease/papain. It is an antibody fragment with molecular weight of about 50,000 and have antigen binding activity, wherein, in the fragment obtained by papain treatment (cleaving H chain at amino acid residue 224), about half of H chain from the N-terminal and the whole L chain are bound together by disulfide bonds. The Fab of the present invention also may be produced by inserting DNA encoding Fab of the antibody into prokaryotes expression vectors and/or eukaryotes expression vectors.

Fab' is an antibody fragment with antibody binding activity, produced by cleaving disulfide bonds in (Fab')2 hinge region, with molecular weight of about 50,000. The Fab' of the present invention also may be produced by inserting DNA encoding Fab' of the antibody into prokaryotes expression vectors and/or eukaryotes expression vectors, and subsequently introducing the vectors into prokaryote and/or eukaryote to express Fab'.

(Fab')2 is an antibody fragment with antigen binding activity, with molecular weight of about 50,000, wherein, in the fragment obtained by protease/pepsin treatment (cleaving H chain at amino acid residue 234) of IgG antibody, the antibody fragment of Fab by bound together with disulfide bonds in hinge region is slightly larger. The (Fab')2 of the present invention may be produced by treating antibody with pepsin. Besides, the (Fab')2 of the present invention also may be produced by linking Fab' with thioether bonds or disulfide bonds.

ScFv is an antibody fragment with antigen binding activity, consisting of a chain $V_H$ and a chain $V_L$ which are connected by appropriate peptide joints. The scFv of the present invention may be produced by obtaining cDNAs encoding $V_H$ and $V_L$ of the antibody, constituting DNA encoding scFv, inserting the DNA encoding scFv into prokaryotes expression vectors and/or eukaryotes expression vectors, and subsequently introducing the vectors into prokaryote and/or eukaryote to express scFv.

Nucleic Acid

The nucleic acids of the present invention are nucleotide sequences encoding at least one of SEQ ID NO: 1-16, specific fragments, variants thereof, or at least 70-100% continuous amino acid sequences of consensus sequences. The nucleic acid molecules encoding at least one anti TNF antibody may be obtained by the methods described in present invention or known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

As indicated herein, nucleic acid molecules of the present invention which comprise a nucleic acid encoding an anti-TNF antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

The nucleic acids of the present invention can be made using (a) recombinant methods, (b) synthetic techniques, (c) purification techniques, or combinations thereof, as well-known in the art.

The nucleic acid compositions of the present invention, such as RNA, cDNA, genomic DNA, or any combination thereof, can be obtained from biological sources using any number of cloning methodologies known to persons skilled in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to persons skilled in the art.

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Persons skilled in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

The isolated nucleic acids of the present invention can also be prepared by direct chemical synthesis by known methods. Chemical synthesis generally produces a single-stranded oligonucleotide, which can be converted into double-stranded DNA by hybridization with a complementary sequence, or by polymerization with a DNA polymerase using the single strand as a template.

Construction of Humanized Monoclonal Antibody Expression Vector

5' fragment is obtained by using a plasmid (pHu-V$_H$) comprising humanized antibody heavy chain variable region V$_H$ gene fragment as template, 5' primer FVHX (5'-CGCG-CAAG-CTTCCTCGAG-3' SEQ ID NO: 17) and 3' primer RVCG (5'-CGATGGGCCCTTGGTGGA-3' SEQ ID NO: 18), which comprises the gene for humanized antibody heavy chain variable region (V$_H$) and 7 amino acid at 5'-teminal of human IgG$_1$ heavy chain constant region (C$_{γ1}$). Meanwhile, A gene comprising human IgG$_1$ heavy chain constant region (C$_{γ1}$) encoding sequence is obtained from RNA prepared from human leucocyte by using 5' primer HuCGF (5'-ACCAAGGGCCCATCGGTCTTC-3'; SEQ ID NO: 19) and 3' primer HUCGE (5'-CGGAATTCTCATTTACCCGGAGA-CAGGGA 3', SEQ ID NO: 20) through reverse transcription and PCR. Finally, the fragment of humanized antibody heavy chain variable region and human C$_{γ1}$ gene are linked by PCR using 5' primer (FVHX, SEQ ID NO: 17) and 3' primer (HUCGE, SEQ ID NO: 20) to obtain a gene fragment of length about 1400 bp comprising heavy chain encoding sequence. The gene fragment is treated with endonuclease Hind III and EcoR1, and then inserted into vectors such as PUC19 (ref: Yanisch-Perron, C., Vieira, J. and Messing, J. (1985) Gene, 33, 103-119).

5' fragment is obtained by using a plasmid (pHu-V$_L$) comprising humanized antibody light chain variable region V$_L$ gene fragment as template, 5' primer FVHX (SEQ ID NO: 17) and 3' primer VKCKO (5'-AGA TGG TGC AGC CAC AGT TCG CTT GAT CTC CAG CTT GGT GCC-3' SEQ ID NO: 21), which comprises the gene for humanized antibody light chain variable region (V$_L$) and 7 amino acid at 5'-teminal of human κ light chain constant region (Cκ). Meanwhile, A gene comprising human κ light chain constant region (Cκ) encoding sequence is obtained from RNA prepared from human leucocyte by using 5' primer HuCKF (5'-GTG GCT GCA CCA TCT GTC TTC-3' SEQ ID NO: 22) and 3' primer HUCKB (5'-TGC GGA TCC CTA ACA CTC TCC CCT GTT GAA-3', SEQ ID NO: 23) through reverse transcription and PCR. Finally, the fragment of humanized antibody light chain variable region and human Cκ gene are linked by PCR using 5' primer (FVHX, SEQ ID NO: 17) and 3' primer (HUCKB, SEQ ID NO: 23) to obtain a gene fragment of length about 700 bp comprising light chain encoding sequence. The gene fragment is treated with endonuclease Hind III and Bam H1, and then inserted into vectors such as PUC19 (ref: Yanisch-Perron, C., Vieira, J. and Messing, J. (1985) Gene, 33, 103-119.).

The cDNA encoding the heavy chain or light chain or the cDNA encoding their modified products which are obtained by aforesaid methods are inserted into pcDNA3 (Invitrogen USA, Carlsbad, Calif., U.S.A.) vector to construct Hu_anti-TNFα humanized expression vector. The expression vector plasmid comprises cytomegalovirus early gene promoter-enhancer required for high level expression in mammal cells. Meanwhile, the vector plasmid also comprises optional maker gene, so as to have amicillin resistance in bacteria, have G418 resistance in mammal cells. Furthermore, the vector plasmid comprises DHFR gene. In suitable host cells, chimeric antibody gene and DHFR gene can be co-amplified by Methotrexate (MTX, Sigma) (see, for example, Axel, R., et al. U.S. Pat. No. 5,179,017; Kaufman, R. and Sharp, P., J. Mol. Biol. 159:601-621, 1982).

Antibody Host Cell

The present invention also relates to produce at least one anti TNF antibody by using recombinant vector gene engineered host cell, and recombinant technique in the art.

Polynucleotides may be optionally linked to vector comprising optional labels, for amplification in the host. generally, the plasmid vector is introduced into a precipitate, such as calcium phosphate, or introduced into complex comprising charged lipid.

Appropriate culture mediums and conditions for the above-described host cells are known in the art. Suitable vectors will be readily apparent to persons skilled in the art. Introduction of a vector construct into a host cell can be effected by calcium phosphate transfection, DEAE-dextran mediated transfection, cationic lipid-mediated transfection, electroporation, transduction, infection or other known methods.

The host cells for the humanized anti tumor necrosis factor monoclonal antibody of the present invention are derived from Chinese hamster ovary cells, which are obtained by transfection with plasmid comprising anti-TNFα gene code, and followed by a series of stringent, specified screening, which including drug screening, gene amplification, and single cell cloning to produce the fanal cell strain. The host cell of the present invention, Chinese hamster ovary cell strain CHO HUAT 132 was deposited at CCTCC at Mar. 7, 2011, with Deposit NO. C201117.

The cell of the cell strain can be bred when suspended in serum free medium; when cultivated in 2 L Fermenter, The level of secreted anti-TNFα in medium will not lower than 1 g/L after the cultivation cycle of 16-20 days ends. The anti-TNFα produced by the cell strains is humanized monoclonal antibody.

Activity of Binding to TNFα

The humanized anti tumor necrosis factor monoclonal antibody of the present invention only has specific affinity with recombinant human tumor necrosis factor (rhTNFα, target molecules), but does not crosslinked to any other protein molecules. In competitive assay of affinity to their target molecules, the humanized anti tumor necrosis factor monoclonal antibody of the present invention has been determined to have a similar affinity as Humira.

The humanized anti tumor necrosis factor monoclonal antibody of the present invention also has the activity to neutralize the toxicity of rhTNFα to L929 target cell, and its EC50 is similar to that of Humira, which is between 20.4 ng/mL and 50 ng/mL.

Therapeutic Use

Anti hTNFα antibody can be used to treat and/or prevent hTNFα related diseases, wherein the hTNFα related disease may be, for example, pyaemia, autoimmune diseases, malignant tumor, lung function disorder, transplant rejection, bacterial meningitis, cerebral malaria, AIDS and AIDS related complex (ARC), secondary cytomegalovirus infection after transplantation. The use of the antibody and antibody components of the present invention in treating hTNFα related diseases will be further discussed as follows:

1) Sepsis

The role of tumor necrosis factor in sepsis pathology, and the biological effects thereof includes hypotension, myocardial depression, vascular leak syndrome, organ necrosis (see for example, U.S. Pat. No. 5,231,024). Therefore, the humanized antibodies of the present invention and antibody components can be used for the treatment of any sepsis with clinical background, including septic shock, endotoxic shock, gram-negative sepsis and toxic shock syndrome.

2) Autoimmune Diseases

It has been found that the tumor necrosis factor plays a role in the pathophysiology of a variety of autoimmune diseases, for example, it has been found that TNFα is involved in activating tissue inflammation and lead to joint destruction in rheumatoid arthritis (see, for example, U.S. Pat. No. 5,231,024; Moeller, A. et al. (1990) Cytokine 2:162-169). It also has been found that TNFα is involved in promoting islet cell death in diabetes and mediates the cytotoxicity to oligodendrocyte and induces inflammatory plaques.

Humanized antibodies and antibody components of the present invention can be used to treat autoimmune diseases, especially those associated with inflammation, including rheumatoid arthritis, rheumatoid myelitis, osteoarthritis and gout arthritis, allergy, multiple sclerosis, autoimmune diabetes, autoimmune eye uveitis, and nephrotic syndrome.

3) Malignant Tumors

It has been found that tumor necrosis factor has been found in malignant tumors is involved in inducing cachexia, stimulating tumor growth, enhancing metastatic potential and mediating cytotoxicity. Therefore, the antibodies and the antibody components of the present invention can be used to treat malignant tumors, inhibit tumor growth or metastasis and/or reduce the malignant secondary cachexia. The antibody or antibody component can be systemic or local administrated to the tumor site.

4) Pulmonary Function Disorders

It has been known that the tumor necrosis factor is involved in pathophysiology of adult respiratory distress syndrome (ARDS), including stimulating white blood cell—endothelial cell activation, cytotoxicity-oriented to lung cells and inducing vascular leak syndrome. Thus, the antibody and the antibody components of the present invention can be used to treat lung function disorders, including adult respiratory distress syndrome, chronic pneumonia, pulmonary sarcoidosis, pulmonary fibrosis and silicosis.

5) Intestinal Dysfunction

Human antibodies and antibody components of the present invention can be used to treat intestinal disorders such as idiopathic inflammatory bowel disease, which includes two syndrome, Crohn and ulcerative colitis.

6) Transplantation

It has been found that tumor necrosis factor may be the key mediators of allograft rejection and transplant plants versushost disease (GVHD), and mediates the side effects observed in the inhibition of renal transplant rejection by rat antibody OKT3 whhich is targeted to T-cell receptor CD3 complex (see for example, Suthanthiran, M., and Strom, T B (1994) New Engl J. Med. 331:365-375)

Therefore, the antibody and the antibody components of the present invention can be used to suppress transplant rejection, including allograft and xenograft rejection, and suppress GVHD.

7) Infectious Diseases

The antibodies and the antibody components of the present invention can be used to treat infectious diseases, including bacterial meningitis, cerebral malaria, AIDS and AIDS-related syndrome (ARC), and secondary cytomegalovirus infection after transplantation. They can also be used to reduce infectious diseases related symptoms, including fever and muscle pain caused by infection (eg influenza), and infection secondary cachexia (such as AIDS or secondary ARC).

Analysis and Diagnostic Purposes

The antibody of the present invention can be used in any known analysis method, such as competitive binding assays, direct or indirect sandwich analysis and immunoprecipitation analysis. Zola, Monoclonal Antibodies: Technical Manual "(Monoclone Antibodies; A Manual of Techniques), pp. 147-158 (CRC Press, Inc., 1987).

Competitive binding analysis depends on the ability of marked standard material competing with analyte in the measured sample to bind limit amount of antibody. Amount of the standard material is inversely proportional to the amount of antibody bound with hTNFα in the measured sample. In order to facilitate the determination of the amount of the bound standard material, the antibodies usually are insoluble before or after the competition, so that it will be convenient to separate the bound standard material and the analyte from unbound standard material and analyte separation.

Sandwich analysis involves the use of two antibodies, each bind to different immunogenicity site or epitope on target proteins. In sandwich analysis, the measured sample analyte is bound to the first antibody fixed on the solid phase carrier, and then the second antibody binds to the analyte, thus forming insoluble three-component complex. See U.S. Pat. No. 4,376,110. The second antibody itself can marked with detectable part (direct sandwich assay), or can be detected by using anti-immunoglobulin antibodies labeled with detectable part (indirect sandwich assay). For example, one of the sandwich analysis is ELISA, in which the detectable part is enzyme.

Anti-hTNFα antibodies can also be used in the diagnostic analysis of hTNFα, for example, to detect its expression in specific cells, tissues or serum. This diagnostic method can be used for the diagnosis of causes for autoimmune diseases The antibody usually can be labeled with detectable molecular. Many Markers can be used, and generally they can be classified as follows:

(a) Radioisotopes, such as 111In, 99Tc, 14C, 131I, 125I, 3H, 32P or 35S. Antibodies can be labeled with radioactive isotopes in accordance with the methods described in *Current Protocols in Immunology*, Volume 1 and 2, Coligen eds, Wiley-Interscience, New York, N.Y., the Pubs (1991), in which the radioactivity may be determined by scintillation counting method, and the diseased sites can be located by using immune-flash photography.

(b) Fluorescent marker, such as rare earth chelating agent (europium chelator), or luciferase and its derivatives, rhodamine and its derivatives, dansyl, lissamine, phycoerythrin and Texas Red. Fluorescent marker may be coupled with antibody using the methods described in for example, *Current Protocols in Immunology* mentioned above. Fluorescence can be quantified by fluorometer.

(c) A variety of substrate markers are available, and U.S. Pat. No. 4,275,149 disclosed some of them. The enzymes usually catalyze chemical changes of a variety of chromogenic substrates which can be detected by many techniques. For example, the enzymes catalyze the color changes of the substrates, which can be measured by spectrophotometer, or the enzymes change the fluorescence or chemiluminescence of the substrate. Previously, the technology of quantitative determination of the fluorescence changes has been described. Chemiluminescent substrates are electrically excited due to chemical reactions, and then illuminate. The light emitted can be determined (such as the use of chemical photometer) or provides energy to fluorescent receptors. The enzyme markers include such as luciferase (for example, firefly luciferase and bacterial fluorescence luciferase; U.S. Pat. No. 4,737,456), luciferin, 2,3-dihydrophthalazinediones, malate dehydrogenase, urease, peroxidase such as horseradish peroxidase (HRPO), alkaline phosphatase, b-galactosidase, glucoamylase, lysozyme, sugar oxidase (eg glucose oxidase enzyme, galactose oxidase and glucose-6-phosphate dehydrogenase), heterocyclic oxidases (such as uricase and xanthine oxidase), lactoperoxidase, micro-peroxidase. O'Sullivan describes the technology of conjugating enzymes to antibodies in *Methods for the Preparation of Enzyme-Antibody Conjugates for use in Enzyme Immunoassay (Meth-*

*ods In Enzym.*) (by J. Langone, and H. the Van Vunakis ed.), Academic press, New York, 73:147-166 (1981).

The compositions of enzyme—substrate include, for example:

(i) Horseradish peroxidase (HRP) and hydrogen peroxidase as substrate, wherein, the hydrogen peroxidase oxidize the dye precursor (eg, o-phenylenediamine (OPD) or hydrochloric acid to 3,3,5,5'-tetramethylbenzidine (TMB));

(ii) Alkaline phosphatase (AP) and p-nitrophenyl phosphate as chromogenic substrate;

(iii) b-D-galactosidase anhydrase (b-D-Gal) and chromogenic substrate (for example, nitrophenyl-b-D-galactosidase) or fluorogenic substrate and 4-methyl umbelliferone-b-D-galactosidase.

Persons skilled in the art may know many other enzyme-substrate combinations. Review of these combinations can be found in U.S. Pat. Nos. 4,275,149 and 4,318,980. Sometimes, markers and antibodies are indirectly coupled. Persons skilled in the art also know all kinds of methods to obtain the said compositions. For example, the antibodies may coupled with biotin, and any one of the above three categories of markers can coupled with avidin, or vice versa. Biotin selectively binds to avidin, and the markers can be coupled with the antibody indirectly. Or, to coupled the marker with antibody indirectly, the antibody can be coupled with a small hapten (eg digoxin), while one of the markers of different types can be couple with anti-hapten antibody (eg anti-digoxin antibody). Therefore, the indirect coupling of markers with the antibody is obtained.

In another embodiment of the present invention, it is not necessary to mark the anti-hTNFα antibodies, and its existence can be detected by marked antibody which binds to the hTNFα antibody.

Affinity Purification Kit

The antibodies of the present invention can be used as affinity purification reagents. In this method, the antibody is fixed on solid-phase, for example, Sephadex resin or filter paper by methods known in the art. The fixed antibody contact with hTNFα-containing samples to be purified, and then the carrier is washed with suitable solvents, and the solvent can substantially remove all the other materials expect hTNFα bound with immobilized antibody.

Pharmaceutical Composition and Mode of Administration

The antibody and antibody components of the present invention may be added into pharmaceutical composition suitable for administration to subjects, wherein the pharmaceutical compositions comprise the antibodies of the present invention and pharmaceutically acceptable excipients, and the pharmaceutical excipients include any physiological applicable solvents, dispersion media, antibacterial agents, antifungal agents, isotonic agents, coating, absorption delay agent. The pharmaceutical compositions of the present invention can take various forms, such as liquid semi-solid and solid dosage forms.

The anti-hTNF antibody of the present invention in a pharmaceutically acceptable dosage form can be administrated to human using known methods. The method includes intravenous (for example, intravenous injection of concentrated drug (bolus) or infusion within a period of time), intramuscular, intraperitoneal, cerebrospinal cavity, subcutaneous, intra-arterial, synovial cavity, intrathecal injection, oral, local injections, or inhalation. The antibody can also be appropriately administrated via intratumor, around tumor, inside injury sites, around injury side to obtain local and systemic treatment. Intraperitoneal injection is expected to be particularly useful, for example, for the treatment of ovarian cancer.

In order to prevent or treat diseases, the appropriate dose of the antibody will depend on the type of the disease to be treated as defined above, disease severity and duration of disease, antibody given for prevention or for treatment, previous treatment, and patient history and antibody response, as well as the attending physician's independent judgment. The antibody is suitable for one-off or series doses to the patients.

According to the type and severity of the disease, no matter one dose or several separated doses, or continuous infusion, 1 μg/kg to 50 mg/kg (eg 0.1-20 mg/kg) of the antibody is the initial candidate dose to patients. The typical daily dose or weekly dose is about 1 mg/kg-20 mg/kg or more, depending on the factors mentioned above. As to repeated dose within a few days or more (depending on condition), the treatment should be continued until the disease symptoms have been inhibited as desired. However, the other regimen can also be used. The progress of treatment can easily monitored using conventional techniques and analysis methods.

Product

1) Injection

Another embodiment of the present invention provides a product containing the material used for the treatment of these diseases. The product includes a container and a label. The suitable containers include such as ordinary bottles, medicine bottles, syringes and test tubes. The container can be made of various materials, such as glass or plastic. The container contains the effective composition for the treatment of diseases, and with a sterile entrance (for example, the container can be a plugged intravenous infusion bag or bottle, the stopper can be penetrated using a hypodermic needle). The active ingredient in the composition is anti-hTNFα antibody. The label on the container or associated with the container associated demonstrates the specific conditions treated by the composition. The products can also have another container, which contains a pharmaceutically acceptable buffer, such as phosphate buffer, Ringer's solution and glucose solution. According to business needs or the needs of users, it can include other materials, such as other buffers, diluents, filters, needles, syringes, and instructions.

2) Sustained Release Formulations

The humanized anti-tumor necrosis factor monoclonal antibodies of the present invention can be used for the preparation of sustained-release formulations. The suitable sustained-release formulations include such as semi-permeable matrix body comprising solid hydrophobic polymers of the antibodies, and the matrix body is a tangible object, such as film or microcapsules. The suitable sustained-release matrix body include such as polyesters, hydrogels (for example, poly(methacrylic acid 2-hydroxy ethyl) or polyvinyl alcohol), polylactide (U.S. Pat. No. 3,773,919), L-glutamic acid and L-glutamic acid ethyl ester copolymer, non-degradable ethylene vinyl acetate, degradable lactic acid-ethanol acid copolymer such as Lupron Depot™ (injectable microspheres composed of lactic acid-glycolic acid copolymer and leuprolide acetate), and poly-D-(–)-3-hydroxybutyric acid. Molecular polymers such as ethylene vinyl acetate and lactic acid-glycolic acid enable the release of molecules lasting for 100 days or more, while some hydrogels release proteins in a short period of time. When encapsulated antibodies are retained in the body for a long time, they may become denaturation or cohesion for contacting with water at 37° C., resulting in biological activity decrease and may lead to changes in immunogenicity. Reasonably stable strategy can be designed according to the mechanism. For example, if the condensation mechanism is the formation of intermolecular S—S bond by sulfur-disulfide interchange reaction, the stabilization can be achieved by modifying thiol residues, lyophilizing acidic solutions, controlling moisture content, using suitable additives and designing special polymer matrix composition.

Kit

For convenience, the antibody of the present invention can be provided in the form of kits, that is to say, predetermined amounts of reagents and the instruction for diagnostic analysis are packed together. If the antibody is enzymatic marked, the kit will contain the substrate and cofactors (such as the substrate precursors providing detectable chromophores and fluorophores) required for the enzyme. Besides, it may also include other additives such as stabilizers, buffers (such as blocking buffer or lysis buffer). In order that the provided reagent concentration can achieve the highest sensitivity of the analysis, the relative amounts of various reagents significantly change. Specifically, the reagent can be dry powder, usually in lyophilized powder form, and excipients may be included. They will form a reagent solution with appropriate concentration upon dissolution.

The present invention is further set forth, in connection with following specific embodiments. It should be understood that these embodiments are for illustrating the present invention only, but not be used to limit the scope of the present invention. In the following embodiment, the experimental methods without indicating the specific conditions are usually performed in conventional conditions, for example, the conditions described in Sambrook et al, *Molecular Cloning: Laboratory Manual* (New York; the Cold Spring Harbor Laboratory Press, 1989), or the conditions recommended by the manufacturer.

EXAMPLES

Example 1

Production of Anti-hTNFα Mouse Monoclonal Antibody

1) Immune

Some 7-11 weeks old female Balb/c mice were IP or ID immunized with the recombinant hTNF (rhTNFα, purchased from Pepro Tech Inc.), and the recombinant human TNFα was emulsified using an equal volume of TITERMAX or Freund's complete adjuvant with final volume of 100-400 μL. At 1-7, 5-12, 10-18, 17-25 and/or 21-34 days thereafter, each mouse were IP (1-400 μg) and SC (1400 μg×2) with TNF which was emulsified with equal volume of TITERMAX or incomplete Freund adjuvant. At 12-25 and 25-40 days thereafter, blood samples were collected from the mouse by hip puncture under non-anticoagulant conditions. And the blood coagulates in RT for 1 hour to collect the serum. Titers were determined using TNFα ELA according to known methods. When repeated injections do not lead to increase in titers, fusion was conducted. At this point, 1-400 μg of TNFα diluted in 100 μL of saline can be injected to the mice for last booster shots. Three days later, the mice were sacrificed by breaking cervical vertebrae, and spleens were removed under sterile conditions, and immersed into 10 mL of cold hydrochloric acid buffered saline (PBS) containing 1000 U/mL penicillin, 100 μg/mL streptomycin, and 0.25 μg/mL amphotericin B (PSA). Spleen cells were harvested by sterile perfusing the spleen with PSA-PBS, and counted by trypan blue dye exclusion method, and resuspended in RPMI 1640 medium containing 25 mM Hepes.

2) Serum Test

A plate was coated with 2 μg/mL of TNFα in PBS overnight. After washed with 0.15 M saline containing 0.02% (v/v) Tween 20, each well was blocked for 1 hour using 1% (w/v) BSA in PBS, 200 μL/well. at RT. The plate was immediately used or frozen at −20° C. for future use. 50 μL/well of mouse serum dilutions were incubated at RT for 1 hour on the TNFα coated plate. The plate was washed, and then monitored at RT for 1 hour with of 1:30000 specific diluted 50 μL/well of HRP labeled IgG Fc probe in 1% BSA-PBS, washed again, added 100 μL/well of citrate-phosphate substrate solution (0.1 M citric acid and 0.2 M sodium sulfate, 0.01% $H_2O_2$ and 1 mg/mL OPD) at RT for 15 minutes, then added 25 μL/well termination solution (4N sulfuric acid). And OD values were read at 490 nm with automatic plate spectrophotometric photometer.

3) Cell Fusion

The live spleen cells identified with a high level of anti-hTNFα antibody in serum in the serum test were fused with mouse myeloma cells at the ratio of 1:1 to 10:1. As a non-restrictive example, the spleen cells and myeloma cells were co-precipitation, and resuspended for 30 seconds or more at 37° C. in 1 mL of 50% (w/v) of PEG/PBS solution (PEG molecular weight 1450, sigma). In order to terminate the fusion, 10.5 mL of RPMI 1640 medium containing 25 mM Hepes (37° C.) for 1 minutes or more. The fused cells were centrifuged at 500-1500 rpm for 5 minutes, and then were resuspended in HAT medium (RPMI 1640 medium containing 25 mM Hepes, 10% Fetal the Clone I serum (Hyclone), 1 mM sodium pyruvate, 4 mM L-glutamine, 10 μg/mL of celebration Trappe factors, 2.5% Origen culture supplement (Fisher), 10% of 653 adjusted RPMI 1640/Hepes medium, 50 μM 2-mercaptoethanol, 100 μM hypoxanthine and 16 μM thymidine), and were seeded on 15 pieces of 96-well flat-bottom plates with 200 μL/well. And then the plates were placed in a 37° C. incubator with 5% $CO_2$ and 95% humility for 7-10 days.

Example 2

Qualitative Test of Anti-hTNFα Murine Antibodies

Two kinds of qualitative tests are available for anti-hTNFα antibody. In one test, the antibody and Humira are competitive in binding hTNFα, and the competition is determined. In the other test, the ability of the antibody to neutralize hTNFα is determined in the assay of determining L929 cell toxicity. Following, these two methods and experimental results are described, respectively.

1) Competitive Binding Assay Against Humira

The anti-hTNFα human antibody humira marked with horseradish peroxidase (HRP) was used as a reagent. Elisa plates were coated with rhTNF (50 μl of 0.05 g/mL), and left overnight at room temperature. The coating solution was discarded, and each well was blocked with 1% skim milk in phosphate buffered saline (PBS) for about 0.5 hours, and washed with PBS containing 0.05% Tween 20. And then a mixture of 50 μl of growth medium and 50 μl of HRP labeled humira was added to each well. Unlabeled humira and antibody-free medium were used as positive and negative controls. The method can screen out mouse monoclonal antibody that can highly inhibit the binding of HRP-labeled humira to rhTNFα. The wells in which the binding of HRP-labeled humira and rhTNFα was inhibited Kong were amplified and subcloned, followed by analysis of several mouse monoclonal antibodies which show the inhibition effects, and finally hybridoma cells were screened out. The hybridoma cells were intermediate cultured, and the supernatant was taken for purification, and the mouse monoclonal antibody TM2-11-12 and TM2-6-3. The purified mouse monoclonal antibodies TM2-11-12 and TM2-6-3 were tested in competition binding assays. Even at the concentration up to 1 µg/mL, the mouse antibody TM2-6-3 only competed out about 50% of the binding of humira to hTNFα. Another mouse antibodies TM2-11-12 showed as good competitiveness as unlabeled humira, since at the concentration of about 0.05 µg/mL (equivalent to 3×10$^{-10}$ M), it can compete out about 50% of the binding of humira to hTNFα.

2) Qualitative Test of Anti-hTNFα Murine Antibodies: Determination of In Vitro Activity to Neutralize hTNFα

The biological activities of both anti-hTNFα mouse antibody and chimeric antibody to neutralize hTNFα biological activity can be measured using the L929 cytotoxicity assay as described below. Each well of a 96-well culture plate was injected 7.5×10$^3$ of L929 cells (ATCC) (10$^5$/mL, 75 µl), and was placed in a 37° C., 5% CO$_2$ incubator for 24 hours. The growth medium for L929 cell was RPMI-1640 containing 5% fetal bovine serum (GIBCO). Using another 96-well culture plate, the solution containing anti-hTNFα antibody was ½ serially diluted with RPMI growth medium, and rhTNFα was added to a final concentration of rhTNFα of 5 ng/mL in each sample well. After the plate containing mixtures was placed in a 37° C., 5% CO$_2$ incubator for 2 hours, the mixture of antibody and rhTNFα was added to the L929 cells well. In each line, the concentrations of antibody in each well were in the order of 0.001 to 2 µg/mL. The culture plate was placed in a 37° C., 5% CO$_2$ incubator. When surviving cells were measured 3 days later, 20 µl of PBS containing 2.5 mg/mL 3-(4, 4-dimethyl-thiazole-2-yl)-2,5-diphenyl-tetrazole bromide salt (MIT; purchased from Sigma Biochemicals) was added, and incubated at 37° C. for 4 hours, and then 100 µl of 0.01 N HCl containing 10% sodium dodecyl sulfate (SDS) was added overnight. Subsequently, 540/690 nm optical density was tested for each well. The curve for the degree of optical density and antibody concentration was plotted. IC$_{50}$ were obtained by analyzing the binding curve, wherein, IC50 means a concentration at which 50% of the rhTNFα toxicity to L929 cells can be neutralized. Therefore, IC50 values can be used to compare the abilities of antibodies to inhibit hTNFα cell toxicity. The IC50 values of several anti-hTNFα murine antibody (TM2-11-12, TM2-10-20, TM2-2-2) and of humira were all in the range of 0.01 to 0.04 µg mL, which means they all have similar capabilities to neutralize L929 cytotoxic caused by rhTNFα. The anti-hTNFα mouse antibody TM2-11-12 was selected for further preparation of the chimeric antibody.

Example 3

Cloning of TM2-11-12 Murine Antibody Heavy Chain and Light Chain

1) Cloning of TM2-11-12 Murine Antibody Heavy Chain Variable Region

To design the humanization of murine antibody, DNA fragments containing the murine antibody TM2-11-12 heavy chain and light chain variable region encoding sequences must be obtained at the beginning. RNA was isolated from TM2-11-12 mouse hybridoma cells with RNA purification kit (Invitrogen Corp.), in order to prepare cDNA (GeneRacer kit, Invitrogen, Corp.). By polymerase chain reaction (PCR), using 5' primer (5'-CGACTGGAGCACGAGGACACTGA-3', SEQ ID NO: 24) and 3' primer (5'-TCCAGGGGC-CAGTGGATAGAGAGA-3', SEQ ID NO: 25), heavy chain variable region DNA fragment was isolated from cDNA. 3' primer is homologous antisense to the mouse IgG1 heavy chain constant region. Those obtained DNA fragments were cloned into TOPO TA vector (Invitrogen) and sequenced. The heavy chain variable region amino acid sequence is SEQ ID NO: 34: QVQLVQSGPELKKPGETVKISCKASGYT-FTHYGMHWVKQTPGRSLKWVGWINTYTG EPTY-DADFQGRFTFSLETSTSTAFLQINTLKD-EDLATYFCARYDFDGFDYWGQGTTLT VSS. The amino acid sequences in complementary determining regions are CDR-H1 (SEQ ID NO: 3), CDR-H2 (SEQ ID NO: 4) and CDR-H3 (SEQ ID NO: 5). The definition for complementary determining regions can be found in Kabat E. et al. *Sequences of Proteins of Immunological Interest*, 5th Edition U.S. Department of Health and Human Services, NIH Publication No. 91-3242.

2) Cloning of TM2-11-12 Murine Antibody Light Chain Variable Region

Similar to the PCR method of cloning the heavy chain variable region, using SEQ ID NO: 29 as 5' primer and another 3' primer which is homologous antisense to the mouse immunoglobulin κ light chain constant region (5'-CACTGGATGGTGGGAAGATGGATA-3', SEQ ID NO: 26), light chain variable region DNA fragment was isolated from the cDNA. The obtained DNA fragments were cloned into TOPO TA vector and sequenced. Two types of clones were found. About ¾ of the clones show that part of the nucleotide sequence cannot be translated into readable amino acid sequence (sequences not shown). Such clones were mutated light chain messenger RNA, which cannot encode functional antibody light chain protein. The remaining about ¼ of clones shows the nucleotide sequence which can be completely translated into readable amino acid sequence. Such clones are derived from the functional light chain messenger RNA. Those obtained DNA fragments were cloned into the TOPO TA vector (Invitrogen) and sequenced. The light chain variable region is amino acid sequence SEQ ID NO: 35: ENVLTQSPPIMSASPGEEVTMTCRASS-SITFNYLHWYQQKSGDSPKVWIYSTSNLVSG VPARF-SGSGSGTSYSLTISSVEAEDAATYYC-QQYSDYPYTFGGGTKLEIK. The amino acid sequences in complementary determining region are CDR-L1 (SEQ ID NO: 6), CDR-L2 (SEQ ID NO: 7) and CDR-L3 (SEQ ID NO: 8). The amino acid sequence was used for designing humanized light chain.

Example 4

Humanization Design of Heavy Chain and Light Chain Variable Region

In order to retain the antigen binding activity, all the amino acid sequences within light chain and heavy chain hypervariable regions are still the same as those of TM2-11-12 murine antibody during the humanizing process. The humanization design includes changing amino acid residues within framework regions in accordance with the sequences of human antibody, designing heavy chain variable region and light chain variable region of humanized antibody with a variety of modification, and directed mutating oligonucleotides sites of the antibody heavy chain and light chain variable region sequence by computer simulation technology, so as to increase antibody binding affinity or reduce antibody immunogenicity.

For the humanized antibody heavy chain variable region (SEQ ID NO: 1), within framework region FR-H1, A can be substituted by E at amino acid residue position 16, S can be substituted by T at position 17, I can be substituted by V at position 20; within FR-H2, K can be substituted by R at position 3, G can be substituted by S at position 9; within FR-H3, T can be substituted by V at position 3, E can be substituted by D at position 7, V can be substituted by T at position 10, F can be substituted by Y at position 14, S can be substituted by T at position 19, T can be substituted by V at position 27.

For humanized antibody light chain variable region (SEQ ID NO: 2), within framework region FR-L1, L can be substituted by M at position 11, R can be substituted by E at position 18, M can be substituted by I at position 21; within FR-L2, W can be by L at position 13; within FR-L3, S can be substituted by A at position 4, L can be substituted by V at position 22, A can be substituted by F at position 27.

By introducing at least one of the aforesaid amino acid modifications, a variety of amino acid sequences of several humanized antibody heavy and light chain variable regions are designed. Several amino acid sequences of humanized antibody heavy chain variable region VH and VL are shown in Table 1:

Example 5

Construction of pHu_anti-H1L1- of TNFα Humanized Antibody Expression Vector

1) Construction of Gene for Humanized Antibody Light Chain

First, the gene fragment for humanized antibody light chain variable region (F001VL) is prepared by synthetic method. And the preparation procedures include obtaining the nucleotides sequences by reverse translation from the amino acid sequence of the light chain variable region according to their genetic codons; adding a Kozak sequence and light chain leader sequence at 5' terminal; preparing the gene fragment for light chain variable region by synthetic method. The gene fragment was cloned into appropriate vectors to obtain pHu-VL1 plasmid. Subsequently, 5' fragment is obtained by using a pHu-VL plasmid as template, 5' primer

TABLE 1 amino acid sequences of humanized antibody heavy chain variable region VH and light chain variable region VL

| No. | Amino Acid Sequence | SEQ ID NO: |
| --- | --- | --- |
| E001$V_H$ | QVQLVQSGPELKKPGASVKISCKASGYTFTHYGM HWVKQTPGRGLKWVGWINTYTGEPTYDADFQGR FTFSLETSVSTAFLQINSLKDEDLATYFCARYDFDG FDYWGQGTTLTVSS | 1 |
| E002$V_H$ | QVQLVQSGPELKKPGASVKISCKASGYTFTHYGM HWVKQTPGRGLKWVGWINTYTGEPTYDADFQGR FTFSLDTSVSTAFLQINSLKDEDLAVYFCARYDFD GFDYVVGQGTTLTVSS | 27 |
| E003$V_H$ | QVQLVQSGPELKKPGESVKISCKASGYTFTHYGM HWVKQTPGRGLKWVGWINTYTGEPTYDADFQGR FTFSLETSTSTAYLQINSLKDEDLATYFCARYDFDG FDYWGQGTTLTVSS | 28 |
| E004$V_H$ | QVQLVQSGPELKKPGATVKVSCKASGYTFTHYGM HWVKQTPGRSLKWVGWINTYTGEPTYDADFQGR FTFSLETSVSTAFLQINTLKDEDLATYFCARYDFDG FDYWGQGTTLTVSS | 29 |
| E005$V_H$ | QVQLVQSGPELKKPGASVKVSCKASGYTFTHYGM HWVRQTPGRGLKWVGWINTYTGEPTYDADFQGR FTFSLETSVSTAYLQINSLKDEDLATYFCARYDFDG FDYWGQGTTLTVSS | 30 |
| F001$V_L$ | ENVLTQSPPILSASPGERVTMTCRASSSITFNYLH WYQQKSGDSPKVWIYSTSNLVSGVPSRFSGSGS GTSYSLTISSLEAEDAATYYCQQYSDYPYTFGGGT KLEIK | 2 |
| F002$V_L$ | ENVLTQSPPILSASPGEEVTMTCRASSSITFNYLH WYQQKSGDSPKVWIYSTSNLVSGVPARFSGSGS GTSYSLTISSLEAEDFATYYCQQYSDYPYTFGGGT KLEIK | 31 |
| F003$V_L$ | ENVLTQSPPIMSASPGERVTMTCRASSSITFNYLH WYQQKSGDSPKVLIYSTSNLVSGVPSRFSGSGSG TSYSLTISSVEAEDAATYYCQQYSDYPYTFGGGTK LEIK | 32 |
| F004$V_L$ | ENVLTQSPPILSASPGERVTLTCRASSSITFNYLHW YQQKSGDSPKVWIYSTSNLVSGVPARFSGSGSGT SYSLTISSLEAEDAATYYCQQYSDYPYTFGGGTKL EIK | 33 |

FVHX (SEQ ID NO: 17) and 3' primer VKCKO (SEQ ID NO: 21), which comprises the gene for humanized antibody light chain variable region ($V_L$) and 7 amino acid at 5'-teminal of human κ light chain constant region ($C_κ$). Meanwhile, A gene comprising human κ light chain constant region ($C_κ$) encoding sequence is obtained from RNA prepared from human leucocyte by using 5' primer HuCKF (SEQ ID NO: 22) and 3' primer HUCKB (SEQ ID NO: 23) through reverse transcription and PCR. Finally, the fragment of humanized antibody light chain variable region and human $C_κ$ gene are linked by PCR using 5' primer (FVHX, SEQ ID NO: 17) and 3' primer (HUCKB, SEQ ID NO: 23) to obtain a gene fragment of length about 700 bp comprising light chain encoding sequence. The gene fragment is treated with endonuclease Hind III and Bam H1, and then inserted into vectors such as PUC19 (ref: Yanisch-Perron, C., Vieira, J. and Messing, J. (1985) *Gene*, 33, 103-119.).

2) Construction of Gene for Humanized Antibody Heavy Chain

First, the gene fragment for humanized antibody heavy chain variable region (E001VH) is prepared by synthetic method. And the preparation procedures include obtaining the nucleotides sequences by reverse translation from the amino acid sequence of the heavy chain variable region according to their genetic codons; adding a Kozak sequence and heavy chain leader sequence at 5' terminal; preparing the gene fragment for heavy chain variable region by synthetic method. The gene fragment was cloned into appropriate vectors to obtain pHu-VH1 plasmid. Subsequently, 5' fragment is obtained by using a plasmid (pHu-$V_H$) comprising humanized antibody heavy chain variable region $V_H$ gene fragment as template, 5' primer FVHX (SEQ ID NO: 17) and 3' primer RVCG (SEQ ID NO: 18), which comprises the gene for humanized antibody heavy chain variable region ($V_H$) and 7 amino acid at 5'-teminal of human IgG$_1$ heavy chain constant region ($C_{γ1}$). Meanwhile, A gene comprising human IgG$_1$ heavy chain constant region ($C_{γ1}$) encoding sequence is obtained from RNA prepared from human leucocyte by using 5' primer HuCGF (SEQ ID NO: 19) and 3' primer HUCGE (SEQ ID NO: 20) through reverse transcription and PCR. Finally, the fragment of humanized antibody heavy chain variable region and human $C_{γ1}$ gene are linked by PCR using 5' primer (FVHX, SEQ ID NO: 17) and 3' primer (HUCGE, SEQ ID NO: 20) to obtain a gene fragment of length about 1400 bp comprising heavy chain encoding sequence. The gene fragment is treated with endonuclease Hind III and EcoR1, and then inserted into vectors such as PUC19 (ref: Yanisch-Perron, C., Vieira, J. and Messing, J. (1985) *Gene*, 33, 103-119) to express humanized antibody heavy chain protein. The sequence of the gene fragment has been verified to be correct by DNA sequencing.

3) Humanized Antibody Single-chain Expression Vector

The cDNAs encoding the heavy chain or light chain which are obtained by aforesaid methods are inserted into pcDNA3 (Purchased from Invitrogen USA, Carlsbad, Calif., U.S.A.) vector to construct pHu_anti-H1L1-TNFα humanized expression vector. The expression vector plasmid comprises cytomegalovirus early gene promoter-enhancer required for high level expression in mammal cells. Meanwhile, the vector plasmid also comprises optional maker gene, so as to have amicillin resistance in bacteria, have G418 resistance in mammal cells. Furthermore, the vector plasmid comprises DHFR gene. In suitable host cells, chimeric antibody gene and DHFR gene can be co-amplified by Methotrexate (MTX, Sigma) (see, for example, Axel, R., et al. U.S. Pat. No. 5,179, 017; Kaufman, R. and Sharp, P., J. Mol. Biol. 159:601-621, 1982).

Example 6

The Expression of Humanized Antibodies

The constructed recombinant expression plasmid was transfected into mammalian host cells to express anti-hTNFα humanized antibody. In order to stabilize high level of expression, the preferred host cells are dihydrofolate reductase (DHFR) deficient Chinese hamster ovary (CHO) cells (see, for example, Chasind, L., et al, U.S. Pat. No. 4,818,679). The preferred method of transfection is electroporation, and other methods also can be used including calcium phosphate coprecipitation, lipid transfection and protoplast fusion. In electroporation, Gene Pulser (Bio-Rad Laboratories) set at 250V electric field and 960 μFd capacitor is used, $2×10^7$ cells suspended in 0.8 mL of PBS is added into a cuvette, which also contains 10 μg expression plasmid DNA linearized by using Pvul (TakaRa). After transfection for 2 days, 0.2 mg/mL of G418 and 200 nM methotrexate (methotrexate or MTX) are added. In order to achieve a high level of expression, the transfected humanized antibody gene is co-amplified by using DHFR gene inhibited by MTX drugs. The subcloning transfectants are diluted, and the secretion rates of various cell lines are determined to screen out cell lines with high-level expression of humanized antibody.

Example 7

Study on the Antibodies Neutralizing TNFα Killing Effect on L929 Cell

L929 cells were trypsinized, centrifuged, resuspended in 1640 medium supplemented with 10% FCS, counted, and added to column 1 to 11 of 96-well plated at a certain concentration. And then, an appropriate concentration of TNFα was added to column 1 to 10 in 96-well plates. Respectively, 2-fold gradient dilutions of adalimumab (purchased from Abbott Laboratories), amino acid unmodified chimeric antibody AT(CE)-1, AT132, AT135, AT143, AT151, AT164 prepared in accordance with Examples 5 and 6 were added to row A, B, C, D, E, F, G and H, in a serial of concentrations from low to high (column 1 to 9). And column 10 is TNFα control, column 11 is cell control, and column 12 is medium control. After addition, the plate was placed in a 37° C. carbon dioxide incubator to cultivate. After incubation was completed, color reagent was added, and continued to incubate. And then absorbance was detected by microplate reader. The results were shown in Table 2.

TABLE 2 the antibodies neutralize TNFα killing effect on L929 cell

| Antibody Type | Heavy Chain | Light Chain | $EC_{50}$(ng/mL) |
|---|---|---|---|
| AT132 | E001$V_H$ | F001$V_L$ | 20.4 |
| AT135 | E002$V_H$ | F001$V_L$ | 50 |
| AT143 | E003$V_H$ | F003$V_L$ | 39.8 |
| AT151 | E001$V_H$ | F002$V_L$ | 42.1 |
| AT164 | E002$V_H$ | F003$V_L$ | 45.5 |
| AT(CE)-1 | — | — | 15.2 |
| Humira | — | — | 19.1 |

The results in Table 2 show that humanized antibodies obtained by mutation in FR region still have good activities in neutralizing TNFα. The EC50 of AT132, 20.4 ng/mL, is similar to that of Humira.

Example 8

Study on AT132 Neutralizing TNFα Killing Effect on Human U937 Cells (Human Lymphoma)

U937 cells in good conditions were counted and adjusted to cell concentration of $3.75 \times 10^4$/well with 1640 medium with 10% FCS. And then were added to a 96-well plate, 75 μl/well. The cell culture medium containing 120 ng/mL of TNFα was used to respectively gradient dilute AT132 standard sample and test samples. The concentration in first well was 600 ng/mL, and dilution gradient was 1.5 fold. After dilutions, the samples were added to 96-well plate with 25 μl/well. The plate was incubated for 40 hours in a 37° C. carbon dioxide incubator. After completion of the incubation, each well was added 10 μl of CCK8 color reagent, and incubated for 3 h, detected with microplate reader at 490 nm/630 nm dual-wavelength. A four-parameter curve fitting was performed to obtain ED50 of the standard sample and test samples, and calculate the specific activity (formula: 100%× ED50 of standard sample/ED50 of test samples).

FIG. 1 shows the curve of antibody neutralizing TNFα killing effects of U937 cells The analysis results of FIG. 1 shows that, at extremely low concentrations of AT132, TNFα kills cells. With the concentration of AT132 increases, TNFα killing effects are gradually antagonized. When the concentration of AT132 reaches about 80 ng/mL, TNFα killing effects are completely antagonized. Clearly, it is dose-dependent according to the results of several experiments. The average median effective concentration of AT132 to neutralize 30 ng/mL of TNFα is 24.1 ng/mL.

Example 9

Determination of AT132 Affinity

AT132 affinity was determined by Biacore X100, and analyzed with Biacore X100 kinetics/affinity analysis software. Using indirect capture method, goat anti-human IgG Fc polyclonal antibody was coupled to the surface of CM5 chip as a capture molecule by using Amine Coupling Kit. By calculation, AT132 and Humira as control were respectively diluted to a a certain concentration to be lately used as ligand, and TNFα as the analyte. Analytes were diluted to 5 concentrations, and each concentration as a cycle. First, using HBS-EP buffer to run for three cycles, designing an analyte concentration of 0 concentration to run for two cycles, and finally, designing a repeat analyte concentration to run for a cycle. The whole process ran 11 cycles, and each cycle can draw a curve. The dynamics/affinity data of the measured antibody and humira were analyzed by Biacore X100 kinetics/affinity analysis software.

Results: AT132 dissociation constant (Kd) of $1.19 \times 10^{-11}$M, that is, the affinity constant (Ka) of $8.4 \times 10^{10} M^{-1}$; Humira dissociation constant of $1.08 \times 10^{-10}$M, that is, the affinity constant $9.3 \times 10^9 M^{-1}$.

Example 10

AT132 Binding Activity to Mouse TNFα and Monkey TNFα

On a plate, respectively coat recombinant human TNFα 5 ng/well, mouse TNFα 25 ng/well, and monkey TNFα 5 ng/well at room temperature, and blocked for 1 h, washed. And then 1.8-fold gradient dilutions of AT132 was added with an initial concentration of 250 ng/mL, and incubated at 25° C. for 2 h, washed, HRP-labeled anti-human Fc antibody added, and incubated at room temperature for 1 h, washed, and the substrate solution added as 100 μl/well, placed in dark at 37° C. for 30 min. In accordance with the order of the added color reagents, 0.2 M $H_2SO_4$, 50 μl/well was added to terminate the reaction. Within about 5 minutes after termination, OD values were test at 450 nm/630 nm on a microplate reader, and median effective concentrations were obtained by four-parameter fitting. Compare the binding activities of AT132 to different sources of TNFα.

Mouse TNFα binding activity results show that AT132 does not bind mouse TNFα. Calculation based on coating concentration and AT132 sample concentration suggests that AT132 binding activity to mouse TNFα is at least 1,000 times lower than that to human TNFα.

Monkey TNFα binding activity results show AT132 binding activity to monkey TNFα was about 50% of that to human TNFα.

Example 11

Preparation of Injections

The preparation of AT132, AT135 injection preparation is as follows:

1) Preparation of 20-L Buffer (Equivalent to 20.180 kg Solution with a Density: 1.009 g/mL)

Weighing out the ingredients in the following weight: 240.0 g mannitol, 26.1 g monohydrate citric acid, 6.1 g sodium citrate, 30.6 g dihydrated disodium hydrogen phosphate, 17.2 g dihydrate phosphate monobasic sodium, 123.3 g sodium chloride, 20.0 g sorbitan polyoxyethylene(20) ether oleate and 19715.7 to 19716.1 g water.

Mixing 40.0 g sodium hydroxide and 1000.8 g water for injection to prepare sodium hydroxide solution.

Then, dissolving following pre-weighted ingredients (as described above) in about 90% water for injection to prepare buffer: mannitol monohydrate citric acid, sodium citrate dihydrate disodium hydrogen phosphate, ether oleate, sodium dihydrogen phosphate, sodium chloride and sorbitan polyethylene(20) ether oleate.

After adding all of the above buffer ingredients, adjusting pH of the solution with 1 M sodium hydroxide prepared by the above method. After adding sodium hydroxide, adding the final weight of water. And then, The buffer is filtered into a sterile container through a filter membrane (hydrophilic poly (vinylidene fluoride), 0.22 μm pore size). The filter media used in the filtration is ammonia for disinfection.

2) Preparation of 40 L Formulation (Equivalent to 40.88 kg)

Filtered buffer solution was added to antibody concentrate (the active ingredient of the pharmaceutical formulation), which has been thawed and merged according to the following methods. Before the preparation of pharmaceutical formulation, the antibody (concentrate) was placed in a water bath to thaw. 34.207 g antibody concentrate was used, which was equivalent to 2.0 kg of protein, protein concentrate with a concentration of 60 mg protein/mL of. The density of the concentrate was 1.0262 g/mL. Any protein concentrate within 25.655-37.316 can be used, which is equivalent to a concentration of 50-80 mg/mL protein in the protein concentrate. Under stirring, the buffer was added until it reaches the final weight of the total solution.

Then, the formulation which comprising all its ingredients was filtered in accordance with the above method except that the formulation was filter by two layers of sterile 0.22 μm

Example 12

AT132 Acute Toxicity Test

Test samples: AT132 lyophilized powder, 20 mg/bottle; adjuvant control: AT132 buffer (containing histidine, trehalose); solvent: sterilized water for injection. Test animal grouping and dose: amount of 60 Kunming (KM) mice, 4-6 weeks old, 18-22 g weight, half male and half female, the SPF level. The animals were randomly divided into three groups, each group of 20, half male and half female. Single dosed and observed for 14 days. Table 3 shows the dose and route of administration:

TABLE 3 dose and route of administration

| No. | Group | Dose in weight (mg/kg) | Dose in volume (mL/kg) |
|---|---|---|---|
| 1 | Adjuvant control | — | — |
| 2 | Test sample, subcutaneous injections | 500 | 25 |
| 3 | Test sample, intravenous injections | 500 | 25 |

Outcome measures: body weight, food intake, mental state, behavior, stool. After the end of the trial observation period, the animals were put euthanasia and pathology gross anatomical observed. And abnormal tissues or organs were histologically examined.

Results: During the trial, no animal died or was dying; all animals were in goold mental state, normal behavior, diet, water drinking, and showed no abnormal performance. The weights of each treatment group animals showed no regular change associated with the administration of dose. Pathology gross anatomy observation showed no abnormal changes related to the administration of dose.

Conclusion: under the present experimental condition, when AT132 powder was administrated to mice by intravenous and subcutaneous injection with a single injection of 500 mg/kg dose, no significant toxicity was observed, and the maximum tolerated dose (MTD) was greater than 500 mg/kg.

Example 13

AT132 Protective Effect on D-galactosamine Sensitized Mouse from rhTNFα-induced Death An amount of 51 C57BL/6 mic, weight 20.0±2.0 g, divided into 6 groups (Table 4). For group 2 to 5, each mouse was intraperitoneally injected 0.25 mL of AT132 solution, wherein, based on the amount of AT132, each mouse in group 2 was given a dose of 5.2 μg/mouse; in group 3, 26 μg/mouse; in group 4, 52 μg/mouse; in group 5, 26 μg/mouse. For group 1, each mouse was intraperitoneally injected 0.25 mL pH 5.63 citrate buffer. For group 6, each mouse was intraperitoneally injected 0.25 mL of human IgG1 (HuIgG1, negative control), 26 μg/mouse based on the amount of HuIgG1. 30 minutes later, every mouse in each group (except group 5) was intraperitoneally injected 0.25 mL mixture solution of rhTNFα (Primegene, batch number 1030109021) and D-galactosamine. For group 5, each mouse was intraperitoneally injected 0.25 mL of buffer. Observed the number of died mice in 48 hours, and calculated survival rates as shown in Table 4.

TABLE 4

The survival rates of mice in each group

| NO. | Group | n | Survival/Total | Survival Rate (%) |
|---|---|---|---|---|
| 1 | Buffer | 9 | 0/9 | 0 |
| 2 | 5.2 μg AT132 | 9 | 3/9 | 33.33 |
| 3 | 26 μg AT132 | 9 | 9/9 | 100 |
| 4 | 52 μg AT132 | 10 | 10/10 | 100 |
| 5 | 26 μg AT132 (No rhTNF) | 7 | 7/7 | 100 |
| 6 | 26 μg HuIgG$_1$ | 7 | 0/7 | 0 |

Results: mice survival rates of buffer and HuIgG1 group were 0. But AT132 protected rhTNFα and D-amino-galactose sensitized mice in dose dependent manner. Therefore, AT132 showed protective effects on D-galactosamine sensitized mice from rhTNFα-induced death.

Example 14

Study on the Effect of AT132 on Type II Collagen-induced Arthritis

An amount of 40 Wistar female rats were randomly divided into 4 groups, and each group is 10 rats. The groups are blank control group, inflammatory control group (model group), AT132 1 mg/kg group, and AT132 5 mg/kg group.

Except for the blank control group, the rats in the other groups were respectively intradermally injected on the back with collagen II immune. And the proinflammatory control group was injected with 0.1 mol/L acetic acid and complete or incomplete Freund's adjuvant emulsion (Sigma, lot number 129K8701).

AT132 1 mg/kg group and AT132 5 mg/kg group began to be intraperitoneal injected with AT132 at the day of immunization. One week after the first immunization, the mice were immunized again in the same way to strengthen the immune, and were administrated for a total of 28 days. At different times before and after administration, rat joint swelling values were measured by YLS-7B toe volume measuring instrument. The joint was taken for pathological examination after the experiments. The swelling rate and inhibition rate were calculated, and the differences between groups were compared by t test. Calculated as follows:

$$\text{Swelling Rate \%} = \frac{E_n - E_0}{E_0} \times 100\%$$

Figure 2:
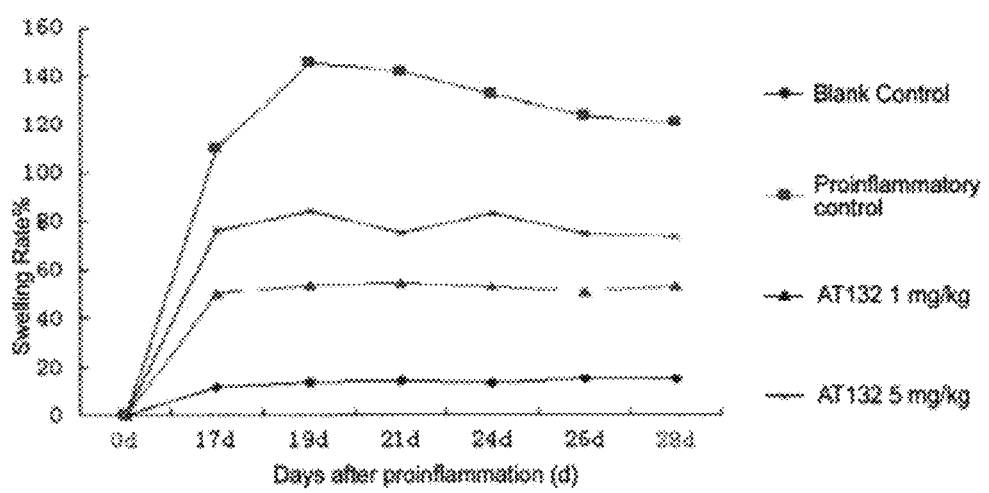
FIG. 2 shows the score of degree of rat joint swelling induced by type II collagen.

$E_n$=swelling values at different times after inflammation,
$E_0$=swelling values before inflammation The experimental data were represented in mean values and standard deviation (s), and t test was used for statistical analysis. The results are shown in FIG. 2. AT132 1 mg/kg group showed significant inhibitory effects, with a good effect starting from day 19, and the best effect is 63.10%. Since then, the inhibitory effect gradually decreased. The result is still good at day 28 with an inhibition rate of 55.71%. AT132 5 mg/kg group showed significant inhibitory effects with significant treating effect starting from day 19. The rat paw joint swelling gradually subsided, and activities became normal, and the effect lasted until day 28 days. The highest inhibition rate of 47.27% appeared at day 21, and the other were about 40%.

Example 15

Pharmacodynamic Study of AT132 on Tg197 Mouse Arthritis Model

The experiment employed Tg197 transgenic mice (purchased from Cyagen Biosciences), and the mice were divided into 6 groups, each group of 10 mice, half male and half female. Specifically as follows: Group 1: AT132 1 mg/kg; Group 2: solvent group (a buffer containing citric acid and sodium chloride); Group 3: AT132 30 mg/kg; Group 4: AT132 10 mg/kg; Group 5: Humira 10 mg/kg; Group 6: AT132 3 mg/kg. Another 4 Tg197 mice were selected as blank control group.

3 weeks old Tg197 mice were intraperitoneally injected AT132, twice a week, until 10 weeks old. AT132 was diluted to the desired concentration prior to administration, and each group was given a dose of 10 μl/g weight. Observe the degree of mice arthritis, and evaluate pathological scores of mice bare joint, and calculate the inhibition rate based on arthritis scores and pathological scores.

1) Study of AT132 on Tg197 Mouse Arthritis Degree

Mice joint morphological changes were evaluated weekly to assess the degree of arthritis, and the specific arthritis scoring criteria as follows:

0.0=no arthritis (appearance normal, the mice are able to support the body weight, overall flexibility/evade capability normal, maximum grip strength);

0.5=onset of arthritis (joints and paws slight swelling, appearance normal, the mice are able to support the body weight, overall flexibility/evade capability normal, maximum grip strength);

1.0=mild arthritis (joints swelling and deformation, paws swelling, appearance normal, the mice are able to support the body weight, overall flexibility/evade capability normal, maximum grip strength);

1.5=mild to moderate arthritis (joints and paws swelling, deformation, and the last fingers inward deformation, barely able to support the weight, overall flexibility reduced, grip strength decreased);

2.0=moderate arthritis (severe joints, paws and fingers swelling, feet joints deformation, cannot support the upper body weight and fall, disappearance of the overall flexibility, grip strength disappeared, crawling/eating affected);

2.5=moderate to severe arthritis (severe joints, paws and fingers swelling, feet joints deformation, cannot support the upper body weight and fall, disappearance of the overall flexibility, grip strength disappeared, crawling/eating affected, finger paws deformation, mouse activity impaired);

3.0=severe arthritis (joint stiffness, bending detected and activity severely impaired, the mice are dying).

Figure 3A:
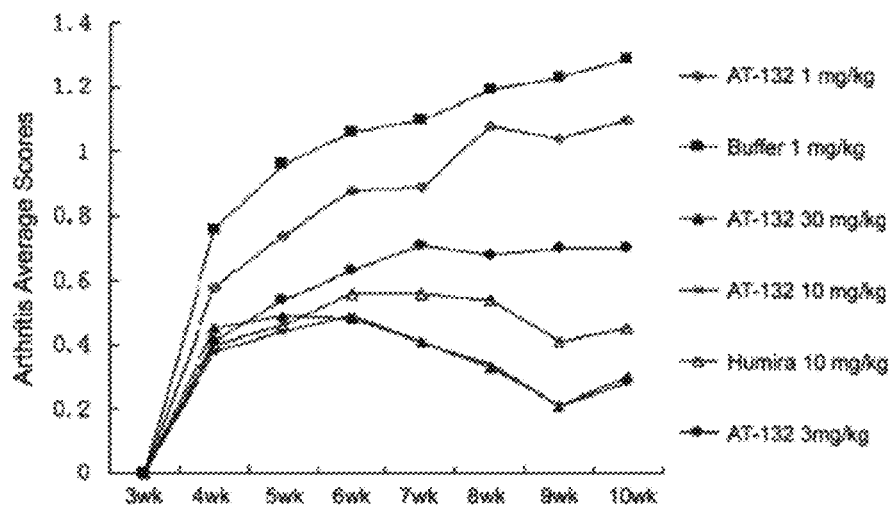
FIG. 3A shows the score of Tg197 mouse arthritis.

Tg197 mice arthritis scores are shown below in FIG. 3A.

2) Tg197 Mice Ankle Joint Histopathology Study

To monitor the disease status, four littermates of Tg197 mice of the trial (Numbered as Con1 to Con4) were sacrificed when 3 weeks old, as joint samples at the beginning of treatment. Experimental mice were sacrificed when 10 weeks old, and sample slices were taken from ankle joints. After hematoxylin/eosin staining, microscopic histopathological scores of arthritis were evaluated in a blinded manner, and the score of 0-4 as follows:

0=no detectable pathology

1=synovial proliferation, polymorphonuclear leukocytes infiltration

Figure 3B:
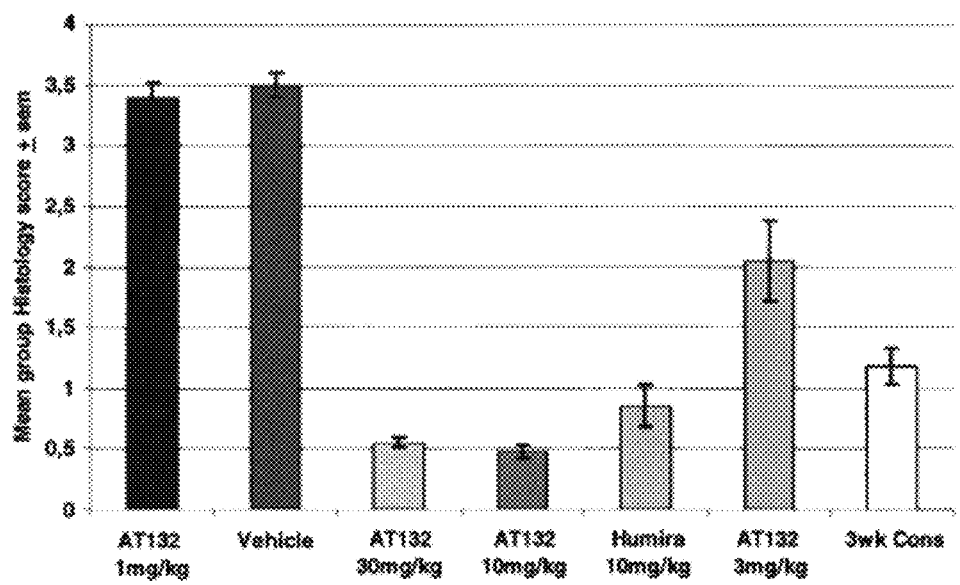
FIG. 3B shows the histology evaluation of treating group of Tg197 mouse.
Figure 3C:
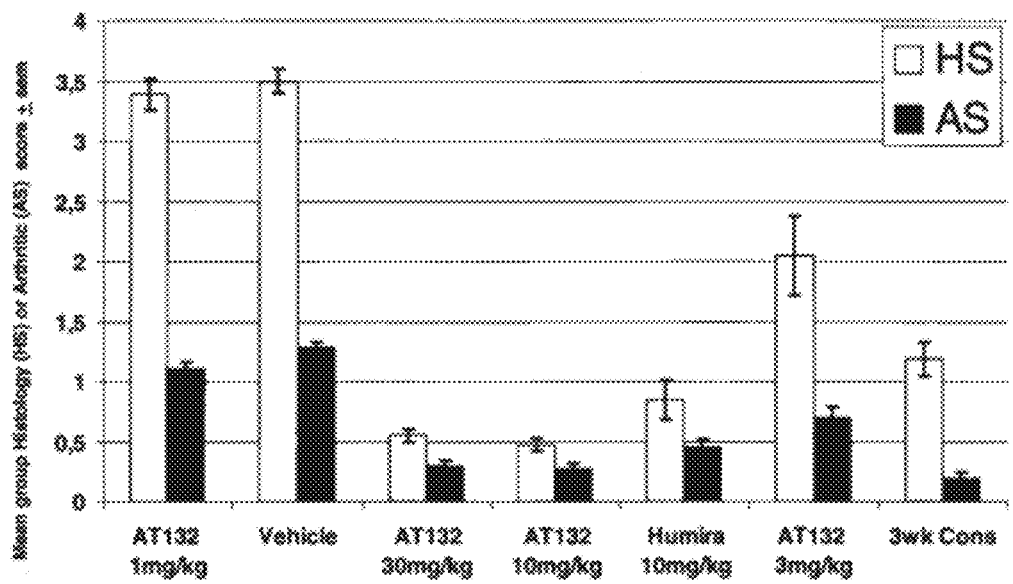
FIG. 3C shows the effect of treating group on arthritis score (AS) and histology score (HS) of Tg197 mouse.

2=pannus and fibrous tissue formation and subchondral bone erosion at focus site 3=cartilage destruction and bone erosion 4=expanded cartilage destruction and bone erosion Tg197 mice histopathological analysis were shown in FIGS. 3B and 3C 3) Calculation of inhibition rates according to the arthritis and pathological scores.

Inhibition rates were calculated according to the arthritis scores as follows:

$$\text{Arthritis Score Inhibition Rate } \% = \frac{E_0 - E_n}{E_0} \times 100\%$$

En=arthritis score of each group
E0=arthritis score of solvent group

Inhibition rates were calculated according to the pathological score as follows:

$$\text{Pathological Score Inhibition Rate } \% = \frac{E_0 - E_n}{E_0} \times 100\%$$

$E_n$=pathological score of each group
$E_0$=pathological scores of solvent group The results are shown in Table 5 below.

TABLE 5 mice arthritis score inhibition rate and pathological score inhibition rate

| No. | Group | n | arthritis score inhibition rate (%) | pathological score inhibition rate (%) |
|---|---|---|---|---|
| Group 1 | AT132 1 mg/kg | 10 | 15 | 3 |
| Group 2 | Solvent | 10 | 0 | 0 |
| Group 3 | AT132 30 mg/kg | 10 | 77 | 84 |
| Group 4 | AT132 10 mg/kg | 10 | 79 | 86 |
| Group 5 | Humira 10 mg/kg | 10 | 65 | 76 |
| Group 6 | AT132 3 mg/kg | 10 | 46 | 41 |

Results: Administrated with different AT132 doses (group 1, group 3, group 4, group 6), it shows significant inhibition effects on rheumatoid arthritis, which is typically dose dependent. Especially from group 1 (1 mg/kg) to group 6 (3 mg/kg), the inhibitions can be significantly distinguished therebetween. From group 6 (3 mg/kg) to group 4 (10 mg/kg), the inhibitions also can be significantly distinguished therebetween. Only between group 4 (10 mg/kg) group and the highest dose group 3 (30 mg/kg), the inhibitions have no difference. It is important that at the same dose level of 10 mg/kg, AT132 treatment group has no significant difference from Humira treatment group 5, and have significantly improvement effect on arthritis histopathology when compared to solvent group 2

Example 16

AT132 Monoclonal Antibody Tissue Cross-reaction

1) AT132 Monoclonal Antibody Human Tissue Cross-reaction

Nasal polyps paraffin slices and four normal human tissue (donor A, B, C, D, provided by National Institutes for Food and Drug Control, and National Center for Safety Evaluation of Drugs) paraffin slices were divided into three groups, namely the experimental group (AT132 biotin marker), positive control group (biotin-labeled Humira), the negative control (buffer PBS). Observe the staining of tissue slicers after tissue cross-reaction.

The experimental results show that the negative control group of human nasal polyps and normal human tissues were not stained. Biotin-Humira positive control group, the human nasal polyps macrophages, the normal human lymph nodes macrophages and the lung alveolar macrophages were weakly to moderately stained, while the other tissues were not stained. Biotin-AT132 experimental group, the human nasal polyps macrophages showed weak to moderate staining. Normal human tissue cross-reactions were similar to Humira.

2) AT132 Monoclonal Antibody Cynomolgus Monkey Tissue Cross-reaction

Nasal polyps paraffin slices and three sets of cynomolgus monkey tissues (donor A, B, C, provided by National Institutes for Food and Drug Control, and National Center for Safety Evaluation of Drugs) paraffin slices were divided into three groups, namely the experimental group (AT132 biotin marker), positive control group (biotin-labeled Humira), the negative control (buffer PBS). Observe the staining of tissue slicers after tissue cross-reaction.

The experimental results show that the negative control group of human nasal polyps and normal cynomolgus monkey tissues were not stained. Biotin-Humira positive control group, the human nasal polyps macrophages were weakly to moderately stained, while the normal cynomolgus monkey tissues were not stained. Biotin-AT132 experimental group, the human nasal polyps macrophages showed weak to moderate staining. Normal cynomolgus monkey tissue cross-reactions were similar to Humira.

What is claimed is:

1. An isolated humanized anti-TNF monoclonal antibody comprising a heavy chain and a light chain, wherein the heavy chain comprises SEQ ID NO: 1, 27, 28, 29, or 30, and the light chain comprises SEQ ID NO: 2, 31, 32, or 33.

2. An isolated nucleic acid comprising a nucleotide sequence which encodes the humanized anti-TNF monoclonal antibody according to claim 1.

3. A vector comprising the nucleic acid according to claim 2.

4. The vector according to claim 3, wherein the vector further comprises a promoter which is operationally linked to the nucleic acid to facilitate its expression.

5. An isolated host cell comprising the vector according to claim 3.

6. A method for preparing a medicament in diagnostic analysis of hTNFα, comprising including in the medicament an effective amount of the humanized anti-TNF monoclonal antibody according to claim 1.

7. A pharmaceutical composition comprising the humanized anti-TNF monoclonal antibody according to claim 1 and at least one pharmaceutically accepted excipient.

8. An isolated humanized anti-TNF monoclonal antibody comprising a heavy chain and a light chain, wherein the heavy chain comprises SEQ ID NO: 1 and the light chain comprises SEQ ID NO: 2.

* * * * *